US012708106B2

(12) United States Patent
Cardoso Bittencourt et al.

(10) Patent No.: US 12,708,106 B2
(45) Date of Patent: Aug. 18, 2026

(54) LANDLESS MONOGASTRIC ANIMAL PRODUCTION SYSTEM

(71) Applicant: DSM IP Assets B.V., Te Heerlen (NL)

(72) Inventors: Leticia Cardoso Bittencourt, Kaiseraugst (CH); Aaron Cowieson, Kaiseraugst (CH); Shelby P. Corray, Kaiseraugst (CH); Thomas J. Frost, Kaiseraugst (CH); Lisa Ann Laprade, Kaiseraugst (CH); Matthew Livingston, Kaiseraugst (CH); Rual Lopez Ulibarri, Kaiseraugst (CH); Estefania Perez Calvo, Kaiseraugst (CH); Yun-Ting Wang, Kaiseraugst (CH)

(73) Assignee: DSM IP Assets B.V., Te Heerlen (NL)

( * ) Notice: Subject to any disclaimer, the term of this patent is extended or adjusted under 35 U.S.C. 154(b) by 1050 days.

(21) Appl. No.: 17/769,096

(22) PCT Filed: Oct. 15, 2020

(86) PCT No.: PCT/EP2020/079115

§ 371 (c)(1),
(2) Date: Apr. 14, 2022

(87) PCT Pub. No.: WO2021/074332

PCT Pub. Date: Apr. 22, 2021

(65) Prior Publication Data

US 2024/0099274 A1 Mar. 28, 2024

(30) Foreign Application Priority Data

Oct. 16, 2019 (EP) .................................... 19203648

(51) Int. Cl.
*A01K 39/012* (2006.01)
*G01N 33/49* (2006.01)

(52) U.S. Cl.
CPC .......... *A01K 39/012* (2013.01); *G01N 33/492* (2013.01)

(58) Field of Classification Search
CPC .... A01K 39/012; A01K 31/22; G01N 33/492; G01N 33/56905; G01N 33/82;
(Continued)

(56) References Cited

U.S. PATENT DOCUMENTS 9,610,314 B1 * 4/2017 Krull ...................... A01N 27/00
2002/0035120 A1 * 3/2002 Cai ......................... A61P 25/00
546/113

(Continued)

FOREIGN PATENT DOCUMENTS

CN 101653198 B * 5/2012 ............ A23K 10/30
CN 104263709 A 1/2015
WO WO-2019121937 A1 * 6/2019 ............ A23K 50/80

OTHER PUBLICATIONS

Slifka et al, "A Survey of Serum and Dietary Carotenoids in Captive Wild Animals", 1999, J. Nutr. 129: 380-390 (Year: 1999).*

(Continued)

*Primary Examiner* — Alex M Valvis
(74) *Attorney, Agent, or Firm* — Banner & Witcoff, Ltd.

(57) ABSTRACT

The present invention relates to a preferably computer-implemented method of raising a group of monogastric animals Issues such as exposure of the animals to an initiator of a disease are recognized at an early stage by ex vivo analysis of blood samples. Said analysis is done where the animals are raised using point-of-care devices. Accuracy of separation between affected and non-affected animals is increased by measuring a set of pre-determined blood parameters. The landless monogastric animal production system of the invention facilitates implementation of the method of the invention.

21 Claims, 6 Drawing Sheets

(58) Field of Classification Search
CPC .. G01N 33/84; G01N 33/50; G01N 2333/465; A23V 2002/00; A23K 20/189; A23K 50/70; A23K 50/75
See application file for complete search history.

(56) References Cited

U.S. PATENT DOCUMENTS

2014/0052463 A1* 2/2014 Cashman .......... G06Q 10/1095 705/2
2018/0312905 A1 11/2018 Igwe et al.

OTHER PUBLICATIONS

Adenaike et al, "Use of discriminant analysis for the evaluation of coccidiosis resistance parameters in chickens raised in hot humid tropical environment", Feb. 5, 2018, Tropical Animal Health and Production 50:1161-1166 (Year: 2018).*
Meluzzi et al., "Determination of Blood Constituents Reference Values in Broilers," Institute of Zooculture, Bologna, Italy, rcvd for publication Apr. 8, 1991; 1992 Poultry Science 71: 337-345.
Polo et al., "Use of ROC curves in clinical and experimental studies." J Vasc Bras. 2020; 19; e20200186. https://doi.org/10.1590/1677-5449.200186.
Nov. 6, 2024—(EP) Office Action—App. No. 20793333.4.
Apr. 21, 2021—(WO) International Search Report and Written Opinion—PCT/EP2020/079115.
Pietro et al., "Biomarkers of Gastrointestinal Functionality in Animal Nutrition and Health," Animal Feed Science and Technology, vol. 250, pp. 9-31 (Apr. 1, 2019).
Rochell et al., "Effects of Eimeria Acervulina Infection Severity on Growth Performance, Apparent Ileal Amino Acid Digestibility, and Plasma Concentrations of Amino Acids, Carotenoids, and α1-Acid Glycoprotein in Broilers," Poultry Science, vol. 95, No. 7, pp. 1573-1581 (Jul. 1, 2016).
Sotirov et al., "Lysozyme and Complement Activities in Broiler-Chickens With Coccidiosis," Revue Med. Vet., vol. 154, No. 12, pp. 780-784 (Jan. 1, 2003).
Livingston et al., "Effects of Broiler Genetics, Age, and Gender on Performance and Blood Chemistry," Heliyon, vol. 6, E04400 (Jul. 11, 2020).
Martin et al., "Selected Blood Chemistry and Gas Reference Ranges for Broiler Breeders Using The i-STAT® Handheld Clinical Analyzer," Avian Diseases, vol. 54, No. 3, pp. 1016-1020 (Sep. 1, 2010).
Cowieson et al., "Effect of Coccidial Challenge and Vaccination on the Performance, Veterinary Postmortem Scores, and Blood Biochemistry of Broiler Chickens," Poultry Science, vol. 99, No. 8, pp. 3831-3840 (Jun. 19, 2020).
Collett, "Chapter 1 Principles of Disease Prevention, Diagnosis, and Control," Diseases of Poultry, 13th Edition, pp. 3-60 (Oct. 4, 2013).
Bilkova Barbora et al, Different breeds, different blood: Cytometric analysis of whole blood cellular composition in chicken breeds, Veterinary Immunology and Immunopathology, May 3, 2017, 71-77, 188, Elsevier.
C Kawashima et al, Effect of ß-Carotene Supply during close up dry period on the onset of first Postpartum Luteal Activity in Dairy Cows, Reprod Dom Anim 45, 2010, e282-e287, 45, Blackwell Verlag GmbH.
Da Silva et al, Broiler chicken responses to immunological stimuli as mediated by different levels of vitamin E in the diet, Poultry Science Association, Inc., 2009, 752-760, 18.
Donal P Conway, Poultry Coccidiosis; Diagnostic and Testing Procedure 3rd edition, Wiley.com, Jun. 2007, 1-19, 3rd edition, Wiley.com.
E D Wills, Mechanism of Lipid Peroxide Formation in Animal Tissues, Biochem J, 1966, 667-676, 99.
H. Steinfeld, A classification of livestock production systems, www.fao.org, Oct. 16, 2019, 1-12, NA.
J Lee, The effect of dietary protein on performance, 2011 Poultry Science, 2011, 1916-1925, 90, Poultry Science Association Inc.
Liebe and White, Analytics in sustainable precision animal nutrition, Feature Article, Apr. 16-24, 2019, 9-2, Animal Frontiers.
N/A, Cartridge and test information, Abbott Point of care, Aug. 15, 2016, 1-6, NA, Abbott Point of care.
N/A, I-Stat Alinity v User Manual_web, User Manual, Jan. 19, 2018, 650-710, NA, Apoc Artwork.
N/A, Introducing our easiest device yet, Alinity-brochure, 1996, 1-12, 42(5), Abott Point of Care Inc.
N/A, PCO2 and calculated values for HCO3, base excess and anion gap, Abbott, Sep. 29, 2017, 1-6, NA, Abbott, Den Haag.
N/A, Vet Scan Avian Reptilian Profile Plus, NA, 2007, 1-57, PN: 500-7131, Abaxis, Inc.
N/A, Vet Scan VS 2—Operator's Manual, Axabis Inc, Feb. 2009, 1-150, NA, Axabis Inc, Union City CA.
RB Williams, A compartmentalised model for estimation of the costs of coccidiosis to the world's chicken production Industry, International Journal for Parasitology, May 31, 1999, 1209-1229, 29, Elsevier.
T.L. Lentfer et al, H/L ratio as a measurement of stress in laying hens—methodology and reliability, British Poultry Science, Apr. 22, 2015, 157-163, 56-2, Taylor & Francis.
Xi Wang, Effects of coccidial vaccination and dietary, Poultry Science Inc, 2019, 2054-2065, NA.

* cited by examiner

| | | Units |
|---|---|---|
| Hematology | Hematocrit (HCT) | % PCV |
| | Hemoglobin (HGB) | g/dL |
| Chemistry | Blood Urea Nitrogen (BUN) | mg/dL |
| | Creatinine | mg/dL |
| | Ionized Calcium (iCa) | mmol/L |
| | Glucose (Glu) | mg/dL |
| Electrolytes | Chloride (Cl) | mmol/L |
| | Sodium (Na) | mmol/L |
| | Potassium (K) | mmol/L |
| Acid Base | pH | |
| | $PCO_2$ | mmHg |
| | $HCO_3$ | mmol/L |
| | $TCO_2$ | mmol/L |
| | Anion Gap | mmol/L |
| | Base Excess | mmol/L |
| Blood Gas | $PO_2$ | mmHg |
| | $sO_2$ | % |
| Specialty | Lactate | mmol/L |

Figure 4

| Analyte | Dynamic Ranges | |
|---|---|---|
| | Common Units | SI Units |
| **AST** | 5-2000 U/L | 5-2000 U/L |
| **BA** | 35 – 200 µmol/L | 35 – 200 µmol/L |
| **CK** | 5-14000 U/L | 5-14000 U/L |
| **UA** | 0.3-25.0 mg/dL | 18-1488 µmol/L |
| **GLU** | 10-700 mg/dL | 0.6-38.9 mmol/L |
| **$CA^{++}$** | 4 -16 mg/dL | 1.0-4.0 mmol/L |
| **PHOS** | 0.2-20.0 mg/dL | 0.06-6.46 mmol/L |
| **TP** | 2-14 g/dL | 20-140 g/L |
| **ALB_BCG** | 1-6.5 g/dL | 10-65 g/L |
| **GLOB*** | 0-13.0 g/dL | 0-130 g/L |
| **K+** | 1.5-8.5 mmol/L | 1.5-8.5 mmol/L |
| **NA+** | 110-170 mmol/L | 110-170 mmol/L |

Aspartate Aminotransferase (AST)

Bile Acids (BA)

Creatine Kinase (CK)

Uric Acid (UA)

Glucose (GLU)

Phosphorous (PHOS)

Calcium ($CA^{++}$)

Total Protein (TP)

Albumin (ALB)

Globulin (GLOB)

Potassium ($K^{+}$)

Sodium ($Na^{+}$)

Figure 5

LANDLESS MONOGASTRIC ANIMAL PRODUCTION SYSTEM

TECHNICAL FIELD

The present invention relates to industrial animal production, and in particular to the meat chicken (broiler) industry.

BACKGROUND OF THE INVENTION

Monogastric animals are raised for various reasons, including egg and meat production. At industrial scale, a farmer is responsible for hundreds or thousands of monogastric animals: the larger the flock, the more efficient mass production is. Whereas economies of scale guarantee more profit, the system also becomes more vulnerable. In the broiler industry for example, economic losses associated with the disease coccidiosis have been estimated to $0.05/bird (Williams, R. B. 1999. A compartmentalized model for the estimation of the cost of coccidiosis to the worlds chicken production industry. Int. J. Parasitol. 29: 1209-1229).

Managing animal health, welfare and performance is of utmost importance in industrial animal production, not only but in particular in the broiler industry.

Nowadays, vaccinations are available for many diseases, including coccidiosis. Whereas coccidiosis vaccination is highly effective in case a flock is indeed exposed to the disease, coccidial vaccination compromises the performance of healthy birds that would not have needed the vaccination. Wang et al. noted that coccidial vaccination reduced the body weight gain (BWG) of broiler chickens from (day) d1-14, d29-42 and from d1-52 (Wang, X., E. D. Peebles, A. S. Kiess, K. G. S. Wamsley and W. Zhai. 2019. Effects of coccidial vaccination and dietary antimicrobial alternatives on the growth performance, internal organ development, and intestinal morphology of *Eimeria*-challenged male broilers. Poult. Sci. 98: 2054-2065). Similarly, Lee et al. noted that coccidial vaccination decreased BW and increased feed conversion ratio (FCR) in broiler chickens (Lee, J. T., N. H. Eckert, K. A. Ameiss, S. M. Stevens, P. N. Anderson, S. M. Anderson, A. Barri, A. P. McElroy, H. D. Danforth, and D. J. Caldwell. 2011. The effect of dietary protein level on performance characteristics of coccidiosis vaccinated and nonvaccinated broilers following mixed-species *Eimeria* challenge. Poult. Sci. 90:1916-1925). Reduced BW in the starter phase in response to coccidial vaccination was also reported by da Silva et al. (Da Silva, I. C. M., A. M. Leal Ribeiro, C. Wageck Canal, C. C. Pinheiro, M. de Moraes Vieira, T. A. Goncalves, R. Alves Pereira and L. Lacerda. 2009. Broiler chicken responses to immunological stimuli as mediated by different levels of vitamin E in the diet. J. Appl. Poult. Res. 18: 752-760). It appears likely that the deterioration in growth associated with coccidial vaccination, especially during the grower phase, is associated with repartitioning of nutrients from lean gains to mount an immune response to the vaccine.

Therefore, a farmer who is responsible for a flock of many thousands of broilers is facing a severe dilemma: If he decides to have the birds vaccinated, profit will be reduced due to the cost for vaccination and due to decreased BWG and/or increased FCR. In other words, profitability is higher if the farm manager decides against vaccination—but only if the flock is not hit by the disease, which is difficult to predict.

There is a need for improving profitability of animal production systems, in particular in the broiler industry.

One approach to increase profitability of industrial animal production is precision animal nutrition. To optimize profitability, the farmer attempts to influence animal's performance by adapting the nutrition to the specific needs of his animals. Whereas this approach seems very promising, it urges the farmer to continuously take decisions.

In case the farmer identifies a sick animal, action must be taken immediately. However, even if the farmer reacts very quickly, the sick animal might already have infected other animals of the same flock. Thus, there is a need to identify arising health issues as early as possible.

In other situations, it is a biological delay that makes decision-making processes difficult and thereby increases the burden of decision making on farmers. For example, if higher nutrient density is provided to correct a nutrient shortfall, it may take days to even weeks to see production response to a new diet (Douglas M. Liebe, Robin R. White, Analytics in sustainable precision animal nutrition, Animal Frontiers, Volume 9, Issue 2, April 2019, Pages 16-24, https://doi.org/10.1093/af/vfz003).

In order to benefit from precision animal nutrition, there is a need to improve the precision of the famer's decision-making processes and to reduce the burden of decision-making on farmers.

SUMMARY OF THE INVENTION

The present invention relates to a method of raising a group of monogastric animals of same species, same breed and preferably same sex, said method comprising the steps:

i) providing venous blood from at least one member of the group,
ii) analyzing the blood provided in step i) to measure the values of at least two pre-determined blood parameters,
iii) adapting feed that is fed to the monogastric animals of the group if the values of the at least two blood parameters measured in step ii) deviate from pre-determined ranges in a pre-determined manner.

The method of the invention allows for early prediction and/or diagnosis of damaging events which could potentially affect the group of monogastric animals from which the blood sample has been taken.

The precision of the prediction and/or diagnosis of a potentially damaging event can be improved by simultaneous use of more than one blood biomarker. In a preferred embodiment, the values of at least three, more preferably of at least four pre-determined blood parameters are measured in step ii).

In a preferred embodiment, the monogastric animals are chicken, preferably broiler chicken. In this embodiment, the method of the invention allows for early prediction of coccidiosis.

Surprisingly, the values of some blood parameters depend on the age of the chicken which the blood sample has been taken from. In a preferred embodiment, at least two, preferably at least three blood parameters are measured in a blood sample taken from a 10 to 20 days old chicken of a group of chicken of same breed and preferably same sex to predict or diagnose coccidiosis in this group.

Due to the earliness of the prediction and/or diagnosis, adequate measures can be taken to mitigate potential loss. Such measures include adaption of the monogastric animals' nutrition. In preferred embodiment, the feed in step iii) of the method of the invention is adapted by adding at least one feed additive. In case coccidiosis is diagnosed or predicted in step ii) of method of the invention, said feed additive comprises preferably one or more microbial muramidases.

Such approach may replace the need for a coccidiosis vaccination. Because coccidiosis vaccination is costly, reduces body weight gain (BWG) and/or increases feed conversion ratio (FCR), profitability may be increased by the method of the invention.

In precision animal nutrition, the famer needs to decide day-to-day what feed is needed in each pen. The burden of decision-making on farmers cannot be overestimated. In some cases, each of the farmer's pen contains a different population: some pens contain younger animals than others; some pens may host a different breed of the same species and yet other pens are in affected by a certain disease whereas others are not. This high degree of complexity makes it impossible that an unexperienced worker or even a robot is taking care of the farm's animals. The need for an experienced farmer who can cope with the burden of every day's decision-making, however, increases cost and therefore decreases profitability of animal production systems.

In a preferred embodiment of the invention, the improved precision of the prediction and/or diagnosis of a potentially damaging event allows to run a farm at least partially by unexperienced workers and/or robots because day-to-day decision making can be run automated. Preferably, the landless monogastric animal production system of the invention liberates the farmer from decision-making as the necessary instructions about what and when needs to be fed is displayed on the farmer's mobile device.

A preferred embodiment of the invention relates to a landless monogastric animal production system comprising:

- at least 1,000 monogastric animals of same species, same breed and preferably same sex and,
- means to draw venous blood from a monogastric animal,
- at least one point-of-care device suitable for measuring the value of blood parameters,
- at least one empty blood collection tube, wherein said tube comprises at least one additive such as heparin or ethylenediaminetetraacetic acid, and
- at least one mobile device, wherein said mobile device is permanently or temporarily connected to at least one point-of-care device.

Even more preferably, the at least one mobile device of the landless monogastric animal production system is permanently or temporarily in communication with at least one supplier of feed additives, premixes and/or feed. In this set-up, the feed additive needed in step iii) of the method of the invention can be ordered at the push of a button or even fully automatically.

The present invention also relates to a computer-implemented method of determining the need of adding an additive to feed that is fed to a group of monogastric animals of same species. Said computer implemented method is based on a model which defines blood parameters that are out of range in case something potentially detrimental has happened or is happening to the animals. Surprisingly, the accuracy of such model can be substantially increased if sex, age and/or breed of the donor the blood sample is taken into account. The accuracy of such model can be further increased if more than one blood parameter is measured.

DETAILED DESCRIPTION OF THE INVENTION

Definitions

The person skilled in the art is familiar with the classification of livestock production systems. In the context of the present invention, the classification of the Food and Agriculture Organization (FAO) is used as published under http://www.fao.org/3/V8180T/v8180T0y.htm. Solely livestock production systems are systems in which more than 90 percent of dry matter fed to animals comes from rangelands, pastures, annual forages and purchased feeds and less than 10 percent of the total value of production comes from non-livestock farming activities. Landless livestock production systems is a subset of the solely livestock production systems in which less than 10 percent of the dry matter fed to animals is farm-produced. A "landless monogastric animal production system" is a subset of the landless livestock production systems, wherein more than 90 percent of livestock are monogastric animals such as chicken.

In the context of the present invention, the term "breed" refers to a stock of animals within a species having a distinctive appearance and typically having been developed by deliberate selection. Thus, the animals are presumably related by descent from common ancestors. By way of example, broiler chicken from the breeds Ross 708 and Cobb 500 can be commercially sourced from local commercial hatcheries.

In the context of the present invention, "raising animals" refers to the production of animals, regardless of the purpose. Thus, "raising animals" includes raising animals for meat and/or egg production. Chicken that are bred for meat production are broiler chicken.

The term "group of monogastric animals" refers to preferably at least 10, more preferably to at least 100 and most preferably to at least 1000 monogastric animals that are raised in the same compartment (e.g. in the same pen or in the same house). A group of monogastric animals "of same age" refers to animals whose birthday is on the same day. In case of birds, "birthday" is the day-of-hatch.

In the context of the present invention, point-of-care testing refers to preferably ex vivo diagnostic testing of a sample at or near the place where the animals are raised (e.g. at or near the chicken farm). A "point-of-care device" is a device that is suitable for performing point-of-care testing.

Sometimes, an anticoagulant is added to a blood sample. Well-known anticoagulants are heparin and EDTA. In the context of the present invention, blood containing heparin is referred to a "heparinized blood".

The value of a "blood parameter" is measurable. By way of example, the blood parameter Na (electrolyte) may have the value 140 mmol ionic sodium per liter blood.

The value of a parameter may depend on the state of a "causal variable". By way of example, the value of the blood parameter Na/sodium on day 13 may be reduced if the respective broiler chicken has faced coccidial challenge. In this example, coccidial challenge causes a reduction of the value of the blood parameter Na/sodium on day 13 and therefore, coccidial challenge is a causal variable.

"Coccidial challenge" refers to an experimental challenge infection wherein at least one monogastric animal is deliberately exposed to an initiator of coccidiosis. Said initiator is preferably a mixture of *Eimeria* species. By way of example, a broiler may face coccidial challenge by receiving the tenfold dose of a coccidial vaccination on a certain day of its life (e.g. on day 1 or day 10). Rather than acting as an immune trigger to provide immunity, the tenfold dose of a coccidial vaccination is likely to cause an infection.

Typically, an infection causes a disease. A "subclinical disease" has no recognizable clinical findings. It is distinct from a "clinical disease", which has signs and symptoms that can be recognized. Many diseases are subclinical before they surface as clinical diseases.

The value of a blood parameter may depend on multiple causal variables such as age and breed.

In the context of the present invention, the causal variable is an independent variable. For illustration purposes, the variation of the causal variable age does most often not depend on the variation of the causal variable breed. Therefore, these two causal variables are independent variables.

One single causal variable may influence the value of more than one blood parameter. By way of example, breed may influence the value of both, the Na/sodium blood parameter and the potassium/K blood parameter. This, however, does not mean that a causal variable influences all known blood parameters. By way of example, breed may influence the Na/sodium and the K/potassium blood parameter, but not the total amount of carotenoids in the blood serum.

There may or may not be a benefit in measuring more than one dependent parameter (e.g. measuring both, the Na/sodium blood parameter and the K/potassium blood parameter). If more than one dependent parameter is measured and if all measured parameters depend on the same independent variable, the amount of information is often not increased. To determine whether it is daytime or nighttime, for example, it is sufficient to measure lightness at a suitable spot in town. Counting the number of people at the same spot in town, in addition to measuring lightness, is not expected to change the conclusion because at nighttime, you typically observe both: less light and less people. However, because both dependent parameters (lightness and number of people) depend on the same independent variable (time of day), the time of day can be deduced more accurately if both dependent parameters (lightness and number of people) are measured.

The expression "pre-determined" refers to something that has been established or decided in advance. By way of example, something may be established or decided in a pre-study, i.e. in a study that is done beforehand. Something that has been determined in such pre-study has been pre-determined and can be used in what is done after the pre-study.

In the context of the present invention, "pre-determined blood parameters" are preferably blood parameters whose values depend on the state of the same given causal variable. This does not apply to all known blood parameters and therefore, the respective pre-determined blood parameters form a subset of all known blood parameters. To find out which blood parameters are influenced by a given causal variable, a pre-study can be done.

The same pre-study also shows if a change of the state of a given causal variable causes an increase or a decrease of the blood parameter's value. Therefore, once the pre-study has been done, the value of the measured pre-determined blood parameter "deviates in a pre-determined manner" from the normal value (baseline) if the state of the selected causal variable is changed.

The same pre-study also shows what the normal value (baseline) of a pre-determined blood parameter is: it is the value measured in the control group (i.e. without intervention/challenge). As in any study, the values measured in the control group will vary within a certain range. Whatever value is within this "pre-determined range" is considered as healthy/normal and therefore, does not require any intervention/action.

Method of Raising a Group of Monogastric Animals

In FIG. 2, a method of raising a group of monogastric animals of same species and same breed is shown. A preferred embodiment of the method of the invention relates to a method of a raising a group of monogastric animals of same species, same breed and same age. An also preferred embodiment of the invention relates to a method of raising a group of monogastric animals of same species, same breed and same sex. The most preferred embodiment of the method of the invention relates to a method of raising a group of monogastric animals of same species, same breed, same age and same sex.

The number of animals in the group of monogastric animals can vary and depends on the species. In a preferred embodiment of the invention, the monogastric animals are birds such as chicken or ducks. Even more preferably, the monogastric animals are broilers. Well known breeds are Ross (e.g. Ross 708) and Cobb (e.g. Cobb 500). Thus, a preferred embodiment of the method of the invention relates to a method of raising a group of birds, preferably chicken, of same species, same breed, same age and/or same sex.

Preferably, the group of monogastric animals are raised in the same compartment, e.g. in the same pen or in the same house. In case the monogastric animals are chicken, a pen typically comprises up to 100 chicken whereas a chicken house may comprise 1,000 or more chicken. Thus, one embodiment of the invention relates to a method of raising a group of monogastric animals of same species, same breed, same age and/or same sex, wherein said group is raised in the same compartment and/or wherein said group comprises more than 10, preferably more than 50, even more preferably more than 100 and most preferably at least 1,000 monogastric animals.

In step ii) of the method of the invention, a blood sample of at least one member of the group of monogastric animals is analysed ex vivo. Whereas it is possible to analyse blood samples of more than one member of the group, it is typically sufficient to analyse a blood sample of only one member of the group. Thereby, the at least one member of the group is preferably selected randomly from the group of monogastric animals. The blood sample analysed in step ii) comprises preferably venous blood. Thus, preceding step i) of the method of the invention comprises preferably the provision of venous blood from at least one member of the group, wherein the method of the present invention is preferably not a diagnostic method practised on the animal body. For preventing blood coagulation in the sample, an anticoagulant such as EDTA or heparin (e.g. sodium heparin) is preferably added to the blood sample. This can be done by using commercially available blood collection tubes. Commercially available tubes for blood sampling are color marked. Commercially available empty purple tubes contain EDTA as an additive whereas empty dark green tubes comprise sodium heparin as an additive.

In step ii) of the method of the invention, the venous blood provided in step i) is analyzed ex vivo. The analysis is preferably done where the animals are being raised, e.g. on the chicken farm. Therefore, at least one point-of-care device is preferably used in step ii). The at least one point-of-care device is preferably a portable device, more preferably a handheld device.

Such devices and corresponding cartridges are commercially available. Often, the type of cartridge determines which blood parameters can be analysed. Some blood parameters can be measured with one cartridge only whereas for measuring other blood parameters, multiple cartridges are available. The total amount carotenoids may be measured with iCheck® carotene photometer device and test kit (BioAnalyt GmbH, Potsdam, Germany). Typically, this is measured in blood serum, i.e. the serum needs first to be separated from the blood. The concentration of electrolytes such as sodium ions and potassium ions may be measured with an i-Stat® Alinity v handheld blood analyzer fitted with a Chem8+ cartridge (Abbott Point of Care Inc., Princeton, NJ) or with a Vetscan® VS2 Chemistry Analyzer (Abaxis, inc) using the Avian/Reptilina Profile Plus cartridge (Abbott Point of Care Inc., Princeton, NJ). This can be done in the whole blood, i.e. without separating the serum from the blood.

Preferably, the decision which blood parameters will be analysed in step ii) has been taken before doing the analysis in step ii).

Pre-Study

If not yet available, a pre-study as shown in FIG. 1 can be done to find pre-determine parameters. In such pre-study, animals are separated into two groups: one group is the control group whereas the other group is exposed to a selected challenge (e.g. heat stress, humidity, nutritional inadequacy, transport stress or exposure to an initiator of a disease). In said pre-study, the values of many blood parameters are measured. The number of blood parameters in the pre-study shown in FIG. 1 is indicated by n. Thus, if 10 different blood parameters are tested in the pre-study, n=10. The same n blood parameters are tested in the control group and the challenged group. Thus, in FIGS. 1, $P_3$ and $P^*_3$ is the same blood parameter (i.e. the third blood parameter), but $P_3$ is measured in the control group whereas $P^*_3$ is measured in the challenged group. In FIG. 1, variable i is the loop counter that controls the iterations of the loop shown in FIG. 1. By way of example, i=3 represents the third blood parameter that is being measured whereas in total n blood parameters are tested. Not all measured blood parameters depend on the selected challenge. In case the value of a parameter is independent of the selected challenge (e.g. does not its change value when exposed to the selected challenge), the corresponding parameter is not indicative for the selected challenge and can therefore be disregarded. In case the value of a parameter depends on the selected challenge (e.g. does change its value when exposed to the selected challenge), the corresponding parameter is indicative for the selected challenge and becomes therefore a pre-determined parameter. Thereby, the selected challenge is the causal variable whose state affects the values of the pre-determined blood parameters. At the end of the pre-study of FIG. 1, all identified pre-determined blood parameters are collected on a list.

In step ii) of the method of raising a group of monogastric animals of the invention, blood parameters are preferably measured whose values depend on the state of the same causal variable. Such blood parameters can be identified by a method for identifying blood parameters whose values depend on the state of the same causal variable, said method comprising the steps:

measuring the values of blood parameters in a blood sample of at least one animal of a control group and measuring the values of the same blood parameters in a blood sample of at least one animal of a group of animals that have been exposed to a challenge, and selecting those blood parameters whose values are increased or decreased in the blood sample of the at least one animal of the group of animals that have been exposed to a challenge when comparing with the values of the corresponding blood parameters in the blood sample of the at least one animal of the control group, and wherein said challenge is preferably selected from the group consisting of heat stress, humidity, nutritional inadequacy, transport stress and exposure to an initiator of a disease and/or wherein the animals of the control group and the animals of the group of animals that have been exposed to a challenge are preferably monogastric animals of same species, same breed, same sex and/or same age.

The thus identified blood parameters are pre-determined blood parameters because the have been determined in a pre-study. A pre-study as shown in FIG. 1 also reveals if the values of the pre-determined blood parameters are increased or decreased in response to the selected challenge. Thus, after having done the pre-study, the pre-determined blood parameters will deviate in a pre-determined manner from the baseline or range. A preferred embodiment of the invention relates to a method of raising a group of monogastric animals of same species and same breed, said method comprising the steps:

i) providing venous blood from at least one member of the group, ii) analyzing the blood provided in step i) to measure the values of at least two pre-determined blood parameters, and iii) adapting feed that is fed to the monogastric animals of the group if the values of the at least two blood parameters measured in step ii) deviate from pre-determined ranges in a pre-determined manner, wherein the values of the blood parameters of step ii) depend on the state of the same causal variable, and wherein said causal variable is preferably selected from the group consisting of heat stress, humidity, nutritional inadequacy, transport stress and exposure to an initiator of a disease.

A particularly preferred embodiment of the invention relates to a method of raising a group of broiler chicken of same breed, same age and/or same sex. Thereby, a pre-study has revealed, that the values of the following blood parameters depend on the exposure or non-exposure to a coccidiosis challenge:

the concentration of sodium ions in preferably heparinized blood, the concentration of potassium ions in preferably heparinized blood, the total amount carotenoids in blood serum.

The above listed parameters are thus pre-determined blood parameters for a coccidiosis challenge. In other words, their values depend on the state of the same causal variable (being exposure or non-exposure to coccidiosis challenge). A pre-study has also shown that the concentration of sodium ions in heparinized blood and total amount carotenoids in blood serum are decreased when the corresponding animal has been exposed to a coccidiosis challenge. In contrast, the concentration of potassium ions in heparinized blood and total amount carotenoids in blood serum is increased when the corresponding animal has been exposed to a coccidiosis challenge.

Thus, a preferred embodiment of the invention relates to a method of raising a group of broiler chicken of same breed, same age and/or same sex, said method comprising the steps:

i) providing venous blood from at least one member of the group, ii) analyzing the blood provided in step i) to measure the values of at least the following three pre-determined blood parameters:

the concentration of sodium ions, preferably after having heparinized blood provided in step i), the concentration of potassium ions, preferably after having heparinized blood provided in step i), the total amount carotenoids in blood serum which as been separated from blood provided in step i).

iii) adapting feed that is fed to the monogastric animals of the group
 if concentration of sodium ions measured in step ii) is below a pre-determined range, and
 if the concentration of potassium ions measured in step ii) is above a pre-determined range, and
 if the total amount carotenoids measured in step ii) is below a pre-determined range.

Surprisingly, the degree of response to a change of state of the respective causal variable depends, at least for some pre-determined blood parameters, on the age of the animal whose blood is analysed in step ii). In case of broiler chicken, the effect of a coccidiosis challenge on the pre-determined blood parameters (such as concentration of potassium ions and sodium ions) is most pronounced if a blood sample of a 13 days old broiler chicken is analysed. The change in concentration of potassium ions and sodium ions can also be detected if a blood sample of a broiler chicken that is younger or older than 13 days is analysed. However, a more sensitive device might be needed to detect such change.

Thus, a particularly preferred embodiment of the invention relates to a method of raising a group of broiler chicken of same breed, same age and optionally same sex, said method comprising the steps:

i) providing venous blood from at least one member of the group,
ii) analyzing the blood provided in step i) to measure the values of at least the following three pre-determined blood parameters:
 the concentration of sodium ions, preferably after having heparinized blood provided in step i),
 the concentration of potassium ions, preferably after having heparinized blood provided in step i),
 the total amount carotenoids in blood serum which as been separated from blood provided in step i).
iii) adapting feed that is fed to the monogastric animals of the group
 if concentration of sodium ions measured in step ii) is below a pre-determined range, and
 if the concentration of potassium ions measured in step ii) is above a pre-determined range, and
 if the total amount carotenoids measured in step ii) is below a pre-determined range, wherein the blood provided in step i) originates from a broiler chicken having an age between 9 and 21 days and having preferably an age of 13 days.

The same principle applies to other monogastric animals, i.e. the age of the animal whose blood is analysed in step ii) may also matter for different species and/or different causal variables. The age of the animal that is most suitable for diagnosis can be revealed in a pre-study and is therefore referred to as pre-determined age; it is not necessarily 13 days.

A preferred embodiment of the invention relates to a method of raising a group of monogastric animals of same species, same breed, same age and optionally same sex, said method comprising the steps:

i) providing venous blood from at least one member of the group,
ii) analyzing the blood provided in step i) to measure the values of at least two pre-determined blood parameters,
iii) adapting feed that is fed to the monogastric animals of the group if the values of the at least two blood parameters measured in step ii) deviate from pre-determined ranges in a pre-determined manner.

wherein the blood provided in step i) originates from a monogastric animal which has just reached a pre-determined age, and/or wherein the values of the blood parameters of step ii) depend on the state of the same causal variable, and/or wherein said causal variable is preferably selected from the group consisting of heat stress, humidity, nutritional inadequacy, transport stress and exposure to an initiator of a disease.

In step iii) of the method of the invention, action is taken if the analysis in step ii) has shown that there is a need to do so (cf. FIG. 2). The purpose of the action taken in step iii) is to mitigate any negative effect the respective causal variable might have. Said action might anything including an adaption of the feed that is fed to the monogastric animals of the group. Thereby, feed might be adapted in any suitable manner. Preferably however, the feed in step iii) is adapted by adding a feed additive or by changing the feed additive that has been added so far.

Surprisingly, the negative effect of coccidiosis can be mitigated by adding in step iii) an additive to the feed, wherein said feed additive comprises preferably one or more microbial muramidases, which is preferably microbial muramidase that is obtained or obtainable from phylum Ascomycota, or subphylum Pezizomycotina.

Therefore, the most preferred embodiment of the invention relates to a method of raising a group of broiler chicken of same breed, same age and optionally same sex, said method comprising the steps:

i) providing venous blood from at least one member of the group,
ii) analyzing the blood provided in step i) to measure the values of at least the following three pre-determined blood parameters:
 the concentration of sodium ions in preferably heparinized blood,
 the concentration of potassium ions in preferably heparinized blood,
 the total amount carotenoids in blood serum.
iii) adapting feed that is fed to the monogastric animals of the group
 if concentration of sodium ions in preferably heparinized blood is below a pre-determined range, and
 if the concentration of potassium ions in preferably heparinized blood is above a pre-determined range, and
 if the total amount carotenoids in blood serum is below a pre-determined range, and wherein the blood provided in step i) originates from a monogastric animal having an age between 9 and 21 days and having preferably an age of 13 days, and wherein in step iii) a feed additive is added to the feed, and wherein said feed additive comprises preferably one or more microbial muramidases, which is preferably microbial muramidase that is obtained or obtainable from phylum Ascomycota, or subphylum Pezizomycotina.

Computer-Implemented Method of Determining the Need of Adding an Additive to Feed that is Fed to a Group of Monogastric Animals The herein described method of raising a group of monogastric animals is preferably done using a computer. Therefore, the present invention also relates to a computer-implemented method of determining the need of adding an additive to feed that is fed to a group of monogastric animals of same species, said method comprising:

providing the values of blood parameters that have been measured ex vivo in the blood of at least one member of the group of monogastric animals;

providing a model which defines blood parameters that are out of range in case a monogastric animal of said species has suffered heat stress, humidity, nutritional inadequacy or transport stress or has been exposed to an initiator of a disease;

using said model to determine if the group of monogastric is in need of an additive that is helpful for a monogastric animal of said species that has suffered heat stress, humidity, nutritional inadequacy or transport stress or has been exposed to an initiator of a disease; and optionally calculating the amount of the additive.

The model used in the computer-implemented method of the invention becomes more accurate when taking into account that the values of some blood parameters depend on age, sex and/or breed. For illustration purposes, reference is made to below table:

| Increasing accuracy of model | | | |
|---|---|---|---|
| variable | pre-determined blood parameter | Result of the study of Example 1 | Conclusions |
| breed | K (electrolyte) | exchanging breed Cobb with breed Roos increases measured K value ($P < 0.01$) | If K value and/or Na value is used in the model, the model should take into account the breed. |
| | Na (electrolyte) | exchanging breed Cobb with breed Roos increases measured Na value ($P < 0.01$) | In contrast, the value of parameter Ca does not change if breed Coob is exchanged with breed Roos. Therefore, if Ca value is used in the model, breed does not necessarily need to be taken into account. |

using said model to determine if the group of birds is in need of an additive that treats or prevents coccidiosis and optionally calculating the amount of the additive, wherein said group of birds is a group of chicken, and wherein said group of birds is preferably a group of chicken of same breed, and wherein said group of birds is more preferably a group of chicken of same breed and of same age, and wherein said group of birds is most preferably a group of chicken of same breed, same age and same sex, and/or wherein said additive is a feed additive that comprises one or more microbial muramidases, which is preferably microbial muramidase that is obtained or obtainable from phylum Ascomycota, or subphylum Pezizomycotina, and/or wherein the values of blood parameters have been measured ex vivo in the blood of a 9 and 21 days old chicken, preferably in the blood of a 10 and 18 days old chicken and most preferably in the blood of a 13 days old chicken.

Therefore, the present invention also relates to a computer-implemented method of determining the need of adding an additive to feed that is fed to a group of monogastric animals of same species, same age, same sex and/or same breed, said method comprising:

providing the values of blood parameters that have been measured ex vivo in the blood of at least one member of the group of monogastric animals, wherein the values of the blood parameters have been measured when the at least one member of the group of monogastric animals has reached a pre-determined age;

providing a model which defines blood parameters that are out of range in case a monogastric animal of said species has suffered heat stress, humidity, nutritional inadequacy or transport stress or has been exposed to an initiator of a disease;

using said model to determine if the group of monogastric animals of same species is in need of an additive that is helpful for a monogastric animal of said species that has suffered heat stress, humidity, nutritional inadequacy or transport stress or has been exposed to an initiator of a disease; and optionally calculating the amount of the additive.

A preferred embodiment of the present invention also relates to a computer-implemented method of determining the need of adding an additive to feed that is fed to a group of birds, said method comprising:

providing the values of blood parameters that have been measured ex vivo in the blood of at least one member of the group of birds;

providing a model which defines blood parameters that are out of range in case a bird suffers from coccidiosis;

An also preferred embodiment of the present invention relates to a computer-implemented method of determining an amount of an additive for a group of birds, said method comprising:

providing the values of blood parameters that have been measured ex vivo in the blood of at least one member of the group of birds;

providing a model which defines blood parameters that are out of range in case a bird suffers from coccidiosis;

using said model to determine if the group of birds is in need of an additive that treats or prevents coccidiosis; and calculating the amount of the additive, wherein said group of birds is a group of chicken, and wherein said group of birds is preferably a group of chicken of same breed, and wherein said group of birds is more preferably a group of chicken of same breed and of same age, and wherein said group of birds is most preferably a group of chicken of same breed, same age and same sex, and/or wherein said additive is a feed additive that comprises one or more microbial muramidases, which is preferably microbial muramidase that is obtained or obtainable from phylum Ascomycota, or subphylum Pezizomycotina, and/or wherein the values of the blood parameters have been measured ex vivo in the blood of 9 and 21 days old chicken, preferably in the blood of 10 and 18 days old chicken and most preferably in the blood of 13 days old chicken.

Use of the Invention

The present invention also relates to the use of at least one point-of-care device in the method of the invention. In a preferred embodiment, the invention relates to the use of at least two non-identical point-of-care devices for providing a recommendation about how to raise a group of monogastric animals of same species, same breed and preferably same sex, wherein one of the at least two non-identical point-of-care devices is suitable for measuring electrolytes ex vivo in an blood sample, and wherein the other of the at least two non-identical point-of-care devices is suitable for measuring the total amount of carotenoids in blood serum that has been separated from whole blood.

The output of the method of the invention might be a recommendation to adapt the feed that has so far been fed to the group of animals. Thus, the present invention also relates to the use of at least two non-identical point-of-care devices for providing a recommendation to a farmer or breeder of a group of animals of same species, same breed and preferably same sex, wherein one of the at least two point-of-care devices is preferably suitable for measuring electrolytes in an optionally pre-treated blood sample, and/or wherein one of the at least two point-of-care devices is preferably suitable for measuring the total amount of carotenoids in blood serum.

Landless Monogastric Animal Production System

When implementing the method of the invention e.g. on a chicken farm, animal health and/or productivity can be increased. However, for implementation of the method of the invention, known landless monogastric animal production systems must be modified.

For doing ex vivo diagnostic testing at or near the place where animals are raised (e.g. at or near the chicken farm), a blood sample is preferably taken at the place where the animals are raised. Therefore, the landless monogastric animal production system of the invention comprises preferably means to draw venous blood from a monogastric animal. Furthermore, it comprises preferably at least one empty blood collection tube, wherein said tube comprises at least one additive such as heparin or ethylenediaminetetraacetic acid (EDTA). If blood serum instead of whole blood is to be analysed at or near the place where the animals are raised, the landless monogastric animal production system of the invention may also comprise means to separate serum from whole blood, wherein said means are preferably a device such as a centrifuge.

For ex vivo analysis of blood samples, the landless monogastric animal production system of the invention comprises preferably at least one point-of-care device, more preferably at least two non-identical point-of-care devices. Said devices are preferably portable devices and even more preferably handheld devices. In an even more preferred embodiment of the invention, the landless monogastric animal production system of the invention comprises at least two non-identical point-of-care devices, wherein one of the at least two non-identical point-of-care devices is preferably suitable for the analysis of blood serum and wherein the other of the at least two non-identical point-of-care devices is preferably suitable for the analysis of blood, preferably heparinized blood. Thus, one embodiment of the invention relates to a monogastric animal production system comprising:

- preferably at least 1,000 monogastric animals of same species, same breed and preferably same sex
- means to draw venous blood from a monogastric animal,
- at least two non identical point-of-care devices suitable for measuring the value of blood parameters, and
- at least one empty blood collection tube, wherein said tube comprises at least one additive such as heparin or ethylenediaminetetraacetic acid, wherein preferably one of the at least two non-identical point-of-care devices is suitable for the analysis of blood serum and wherein the other of the at least two non-identical point-of-care devices is suitable for the analysis of blood, preferably heparinized blood.

To facilitate the farmer's or breeder's decision-making process even further, the farmer's or the breeder's cell phone or any other mobile device may be connected to the at least one point-of-care device. Thus, a preferred embodiment of the invention relates to a landless monogastric animal production system comprising:

- at least 1,000 monogastric animals of same species, same breed and preferably same sex
- means to draw venous blood from a monogastric animal,
- at least one point-of-care device suitable for measuring the value of blood parameters,
- at least one empty blood collection tube, wherein said tube comprises at least one additive such as heparin or ethylenediaminetetraacetic acid, and
- at least one mobile device, wherein said mobile device is permanently or temporarily connected to at least one point-of-care device, wherein said system is preferably a farm that introduces at least one ton feed/year from outside the farm, preferably by buying feed from an external supplier.

An also preferred embodiment of the invention relates to a landless monogastric animal production system comprising:

- at least 1,000 monogastric animals of same species, same breed, same age and/or same sex
- means to draw venous blood from a monogastric animal,
- at least one point-of-care device that is suitable for measuring electrolytes in an optionally pre-treated blood sample
- at least one point-of-care device that is suitable for measuring the total amount of carotenoids in blood serum, and
- at least one blood collection tube comprising preferably at least one coagulant, and
- at least one mobile device, wherein said mobile device is permanently or temporarily connected to at least one point-of-care device, wherein said system is preferably a farm that introduces at least one ton feed/year from outside the farm, preferably by buying feed from an external supplier, and wherein said monogastric animals are preferably birds, more preferably broiler chicken.

Set-Up of the Invention

Buying feed from an external supplier can then be automized. By way of example, the famer's cell phone being permanently or temporarily connected to the point-of-care device of landless monogastric animal production system may autonomously order feed or a feed additive from an external supplier to facilitate step iii) of the method of the invention. Thus, a preferred embodiment of the invention relates to a set-up comprising the herein described landless monogastric animal production system and at least one supplier of feed additives, premixes and/or feed, wherein the at least one mobile device of the landless monogastric animal production system is permanently or temporarily in communication with the at least one supplier of feed additives, premixes and/or feed. A preferred embodiment of the set-up of the invention is shown in FIG. 3.

FIGURES

Figure 1:
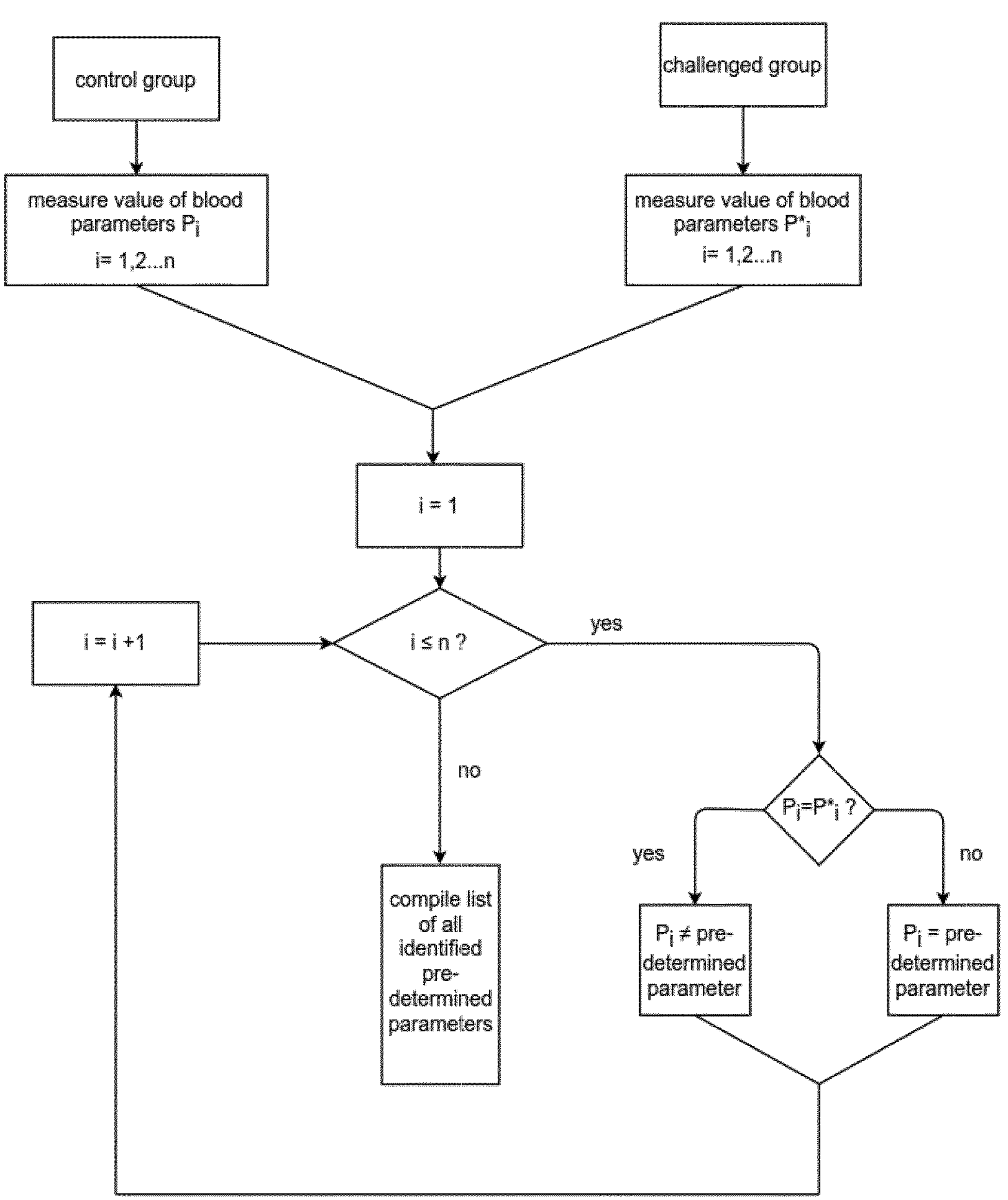
FIG. 1 illustrates how the pre-determined parameters for a given challenge can be found in a pre-study. Such pre-study was done in Example 2.
Figure 2:
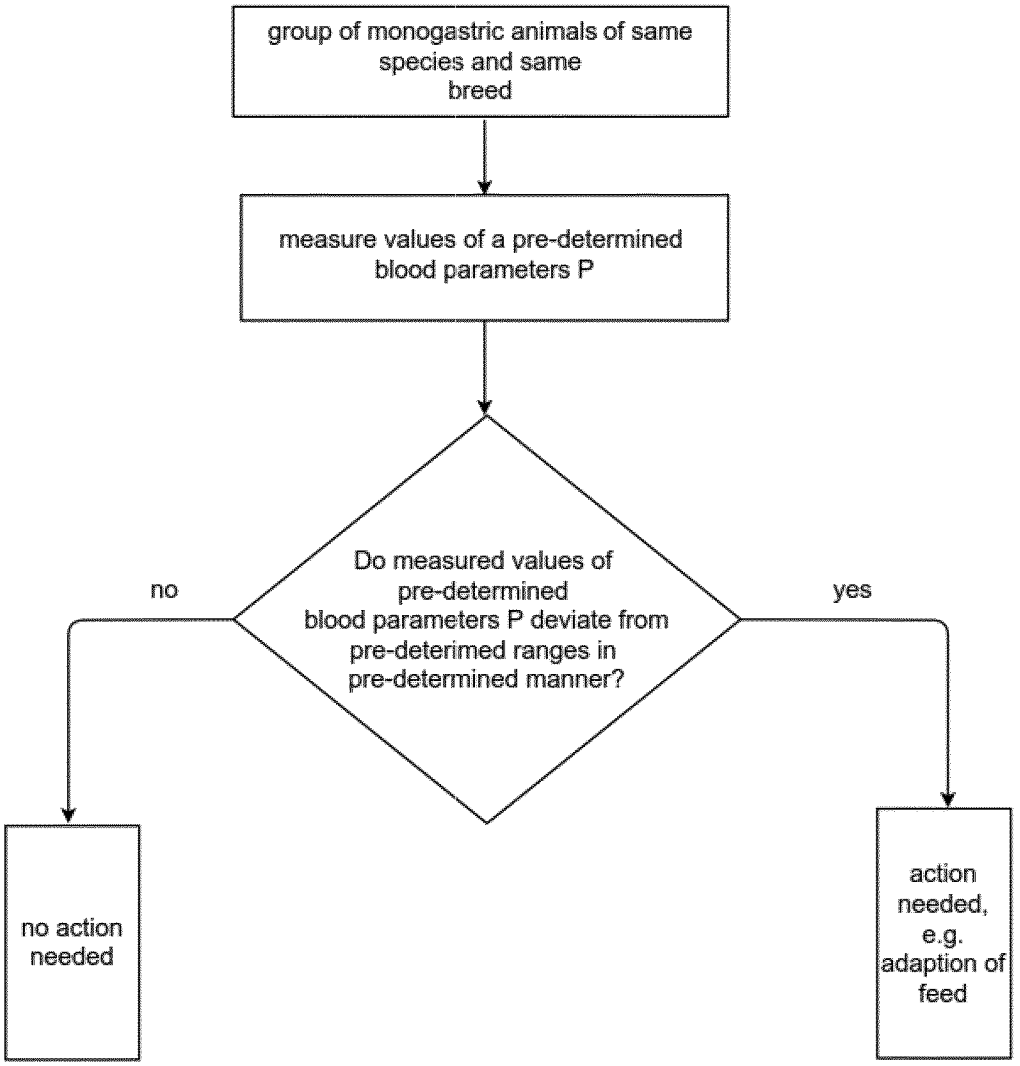
FIG. 2 illustrates the method of the invention. It is a method of raising a group of monogastric animals of same species and same breed.
Figure 3:
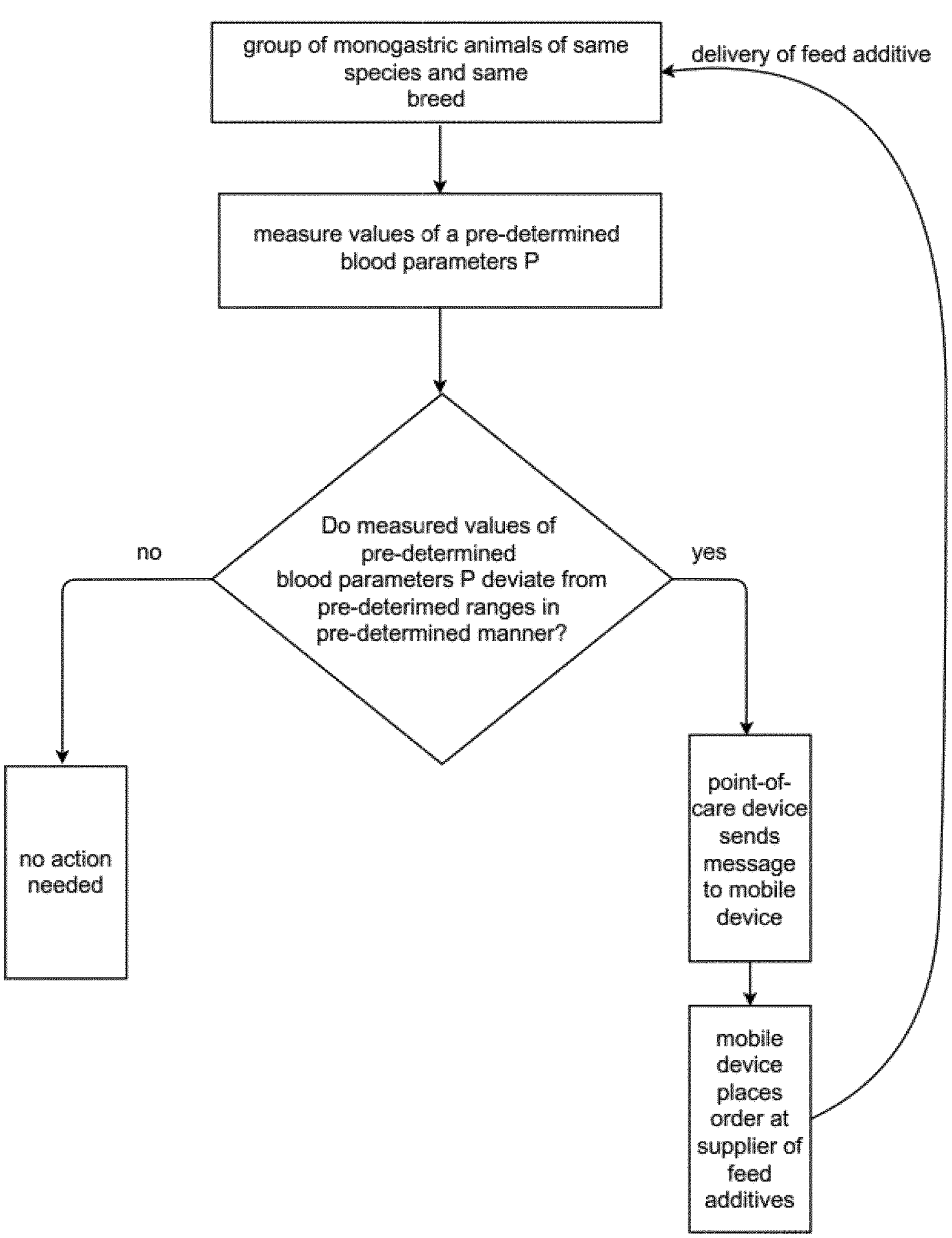

FIG. 3 illustrates a preferred embodiment of the set-up of the invention. The point-of-care device is located where the animals are raised and is connected to a mobile device (e.g. to the chicken farmer's cell phone). If action is needed, the mobile device intervenes by ordering a feed additive that is suitable for mitigating the detected issue. The supplier executes the order by delivering the feed additive to where the animals are raised.

FIG. 4 shows blood parameters that can be measured with i-Stag Alinity v handheld blood analyzer fitted with a Chem8+ cartridge. More detailed information is published in "Cartridge and test information", Rev. Date: 15 Aug. 2016, Art: 714258-010, available at Abbott and in the brochure "Introducing our easiest device yet—i-STAT Alinity", available at Abbott and also downloadable at www.pointofcare.abbott. Additional information can also be found in The User Manual i-STAT Alinity v Analyzer, intended for veterinary use only, 650-7100 Rev. A, Rev Date: 19 Jan. 2018, available at Abaxis, Inc., 3240 Whipple Road, Union City, CA 94587, USA (www.abaxis.com).

FIG. 5 shows blood parameters that can be measured with Vetscan® VS2 Chemistry Analyzer (Abaxis, Inc) using the Avian/Reptilina Profile Plus cartridge. For details, see "Operator's Manual VertScanVS2", dated February 2009, available at Abaxis, Inc., Union City, CA 94587 and in the publication "VetScan® Avian Reptilian Profile Plus", dated March 2007, PN: 500-7131, Rev: D.

Figure 6:
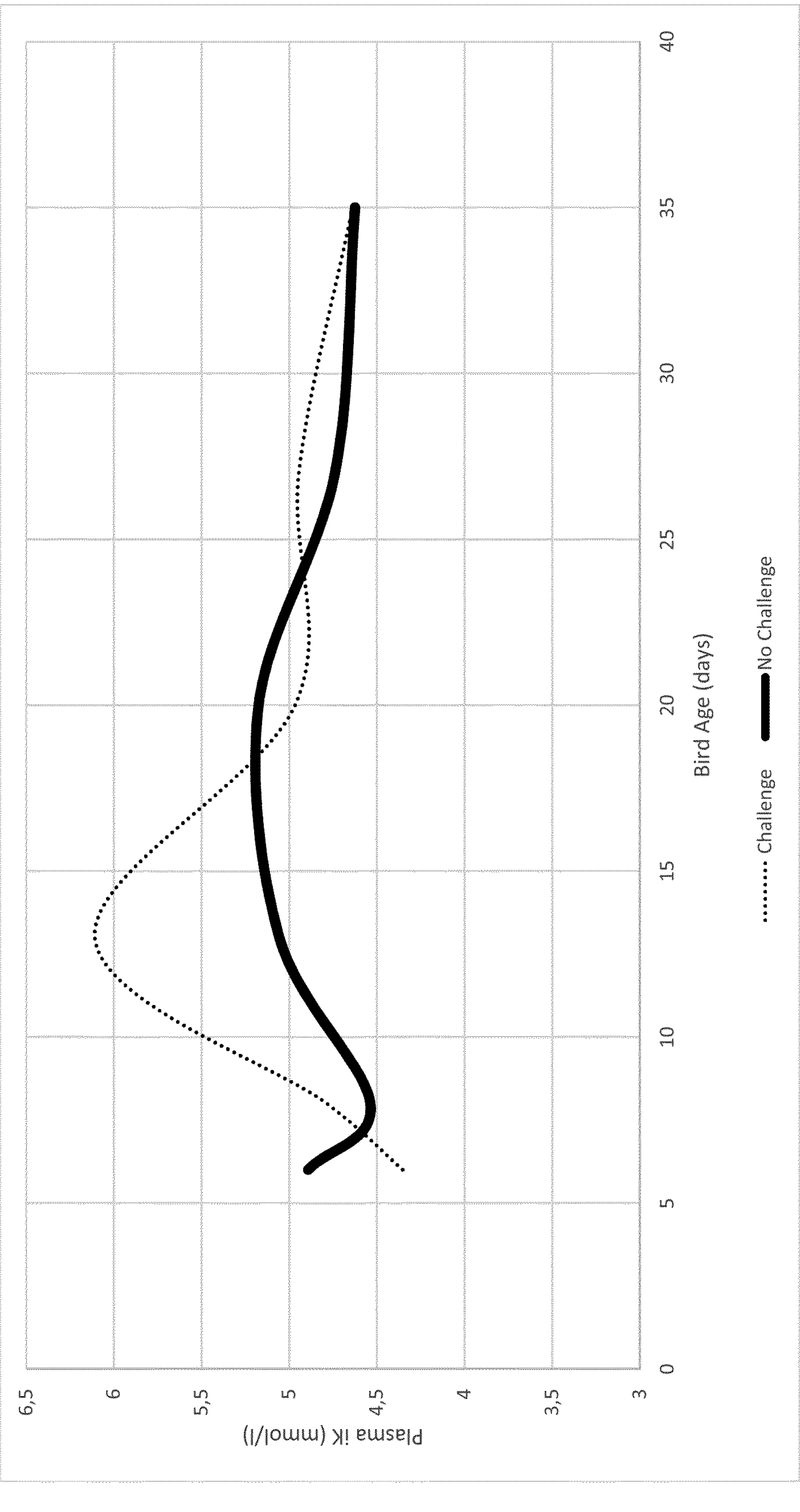

FIG. 6 shows the effect of age and a mixed-species coccidial challenge (introduced on d7) on plasma potassium (K) concentration in male Cobb 500 broiler chickens. A significant age*challenge interaction was observed which was generated by the transient increase around d13.

EXAMPLES

Example 1 (Effect of Age, Sex, and Breed on Blood Parameters)

The study of Example 1 shows which blood parameters of broilers are influenced by age, sex or breed.

A model which defines blood parameters that are out of range in case a chicken suffers from coccidiosis becomes more accurate if the results of the study of Example 1 are incorporated into the model.

Facilities and Rearing

Ross 708 and Cobb 500 chicks were sourced form a local commercial hatchery, vent-sex sorted, individually neck tagged, and allocated into 40 pens according to sex and breed to create a 2×2 factorial arrangement with 10 pens per treatment group. Pens were of uniform size (1.2 m×1.2 m; 1.82 m 2) with 16 chicks per pen in a closed, tunnel ventilated house. Each pen was supplied with one bell water drinker, one tube feeders, and bedded with fresh pine shavings (15 cm deep). All broiler chicks were assigned to the same corn-soy based diet in starter, grower, and finisher phases (cf. below Table 1).

TABLE 1

Composition of broiler starter, grower, and finisher diets

| | Starter[5] | Grower[6] | Finisher[7] |
|---|---|---|---|
| Ingredients | | | |
| Corn | 57.60 | 63.85 | 66.48 |
| Soybean meal (48% CP) | 32.02 | 23.89 | 21.55 |
| Poultry by-product meal | 5.00 | 5.86 | 5.22 |
| Poultry fat | 2.00 | 2.51 | 3.99 |
| Dicalcium phosphate (18.5% P) | 1.24 | 1.16 | 0.67 |
| Limestone | 0.61 | 0.82 | 0.66 |
| Salt | 0.50 | 0.50 | 0.50 |
| Choline chloride (60%) | 0.20 | 0.20 | 0.20 |
| Vitamin premix[1] | 0.05 | 0.05 | 0.05 |
| Mineral premix[2] | 0.20 | 0.20 | 0.20 |
| Selenium premix[3] | 0.05 | 0.05 | 0.05 |
| DL-Methionine | 0.23 | 0.17 | 0.11 |
| L-Lysine | 0.14 | 0.20 | 0.13 |
| L-Threonine | 0.11 | 0.09 | 0.14 |
| Coccidiostat[4] | 0.05 | 0.05 | 0.05 |
| Total | 100.00 | 100.00 | 100.00 |
| Calculated nutrient content | | | |
| Crude protein | 23.00 | 20.00 | 18.50 |
| Calcium | 0.90 | 0.90 | 0.70 |
| Available phosphorus | 0.45 | 0.45 | 0.35 |
| Potassium | 0.88 | 0.93 | 0.72 |
| Total lysine | 1.31 | 1.14 | 1.00 |
| Total methionine | 0.59 | 0.49 | 0.42 |
| Total threonine | 0.88 | 0.76 | 0.76 |
| Total methionine + cysteine | 0.95 | 0.81 | 0.72 |
| Sodium | 0.22 | 0.22 | 0.22 |
| Metabolizable energy (kcal/g) | 2,935 | 3,050 | 3,150 |

[1]Vitamin premix supplied the following per kg of diet: 13,200 IU vitamin A, 4,000 IU vitamin $D_3$, 33 IU vitamin E, 0.02 mg vitamin $B_{12}$, 0.13 mg biotin, 2 mg menadione ($K_3$), 2 mg thiamine, 6.6 mg riboflavin, 11 mg d-pantothenic acid, 4 mg vitamin $B_6$, 55 mg niacin, and 1.1 mg folic acid.

[2]Mineral premix supplied the following per kg of diet: manganese, 120 mg; zinc, 120 mg; iron, 80 mg; copper, 10 mg; iodine, 2.5 mg; and cobalt, 1 mg.

[3]Selenium premix provided 0.2 mg Se (as $Na_2SeO_3$) per kg of diet.

[4]Coccidiostat supplied monensin sodium at 90 mg/kg of food.

[5]Starter diet was fed to approximately 14 d of age, 910 g per bird.

[6]Grower diet was fed from approximately 15 to 35 d of age, 2,750 g per bird.

[7]Finisher diet was fed from approximately 36 to end of experiment.

Performance and Blood Physiology

Broiler BW and feed consumption were recorded at 1, 7, 14, 21, 28, 35, and 42 d[1] of age and FCR calculated. At 14, 21, 28, 35, and 42 d of age two broilers per pen were selected for venous blood analysis. Blood was then analyzed as described in Example 2 (see below).

[1] d=day(s)

Statistical Analysis

Data were analyzed using JMP Pro 14 (available at SAS Institute, Cary, NC 27513-2414, USA GmbH).

Statistical analysis of the study of Example 1 shows that age has a highly significant impact on selected electrolytes (blood calcium, phosphorus, potassium, sodium, chloride), carotene, aspartate aminotransferase, creatine kinase, bile acids, uric acid, total protein, albumin, globulin, total carbon dioxide, hematocrit, and malondialdehyde.

Statistical analysis of the study of Example 1 also shows that sex has a significant impact: male broilers had reduced blood sodium and chloride (electrolytes), carotene, uric acid, albumin, and increased total protein, glucose, and total carbon dioxide.

Statistical analysis of the study of Example 1 also shows that breed has a significant impact: Ross broilers had greater blood potassium and sodium (electrolytes), as well as reduced uric acid, total protein, globulin, and malondialdehyde, compared with Cobb birds.

The model of the present invention can be used to determine if a group of chicken is in need of an additive that treats or prevents coccidiosis. Such model becomes more accurate if the results of the study of Example 1 are taken into account. This can be done by raising a group of chicken of same sex, same breed and same age and by ex vivo analysis of a blood sample that is drawn when the chicken have reached a pre-determined age.

Details of the study of Example 1 are shown in below Tables 2, 3, and 4:

TABLE 2

Effects of breed (Cobb or Ross), sex (Male or Female) and age on blood mineral composition of broiler chickens fed a nutritionally adequate corn/soy-based diet.

| Breed | Sex | Age | $^{v}$Ca (mg/dL) | $^{v}$PHOS | $^{v}$K | $^{v}$Na | $^{i}$Na | $^{i}$K (mmol/L) | $^{i}$Cl | $^{i}$Ca | $^{i}$AnGap |
|---|---|---|---|---|---|---|---|---|---|---|---|
| Cobb | | | 11.52 | 7.27 | 7.36 | 148.1 | 143.6 | 4.93 | 108.3 | 1.36 | 16.2 |
| Ross | | | 11.48 | 7.32 | 8.12 | 149.2 | 144.1 | 4.96 | 108.4 | 1.35 | 16.4 |
| P< | | | NS | NS | <0.001 | NS | 0.011 | NS | NS | NS | NS |
| | Male | | 11.48 | 7.35 | 7.78 | 148.3 | 143.6 | 5.01 | 107.6 | 1.35 | 16.4 |
| | Female | | 11.53 | 7.23 | 7.70 | 149.0 | 144.1 | 4.88 | 109.1 | 1.36 | 16.3 |
| | P< | | NS | NS | NS | NS | 0.015 | NS | 0.009 | NS | NS |
| | | 14 d | 11.43bc | 6.11$^{c}$ | 6.69 | 146.1 | 140.9$^{c}$ | 5.55$^{a}$ | 110.6$^{a}$ | 1.26$^{c}$ | 12.9$^{b}$ |
| | | 21 d | 11.97$^{a}$ | 7.45$^{ab}$ | 7.14 | 149.6 | 144.0$^{b}$ | 5.11$^{b}$ | 108.3$^{ab}$ | 1.39$^{a}$ | 17.2$^{a}$ |
| | | 28 d | 11.26$^{bc}$ | 7.91$^{a}$ | 8.17 | 148.1 | 143.5$^{b}$ | 4.63$^{cd}$ | 107.0$^{b}$ | 1.33$^{b}$ | 16.9$^{a}$ |
| | | 35 d | 11.72$^{ab}$ | 7.26$^{b}$ | 9.07 | 149.5 | 145.5$^{a}$ | 4.52$^{d}$ | 106.7$^{b}$ | 1.39$^{a}$ | 16.8$^{a}$ |
| | | 42 d | 11.13$^{c}$ | 7.74$^{ab}$ | 7.64 | 149.8 | 145.3$^{a}$ | 4.94$^{bc}$ | 108.9$^{ab}$ | 1.39$^{a}$ | 17.8$^{a}$ |
| | | P< | <0.001 | <0.001 | <0.001 | 0.022 | <0.001 | <0.001 | <0.001 | <0.001 | <0.001 |
| | | Linear P< | 0.032 | <0.001 | <0.001 | 0.012 | <0.001 | <0.001 | 0.021 | <0.001 | <0.001 |
| | | Quadratic P< | 0.027 | <0.001 | <0.001 | NS | <0.001 | <0.001 | <0.001 | 0.010 | <0.001 |
| Model Pooled SEM | | | 0.25 | 0.32 | 0.48 | 1.9 | 0.5 | 0.19 | 1.3 | 0.02 | 0.5 |
| Interaction Terms | | | | | | | | | | | |
| Breed*Age | | | NS | NS | 0.005 | NS | NS | NS | NS | NS | NS |
| Sex*Age | | | NS | NS | NS | NS | NS | 0.017 | NS | NS | NS |
| Breed*Sex | | | NS | 0.08 | NS | NS | NS | NS | NS | NS | NS |
| Breed*Age*Sex | | | NS | 0.023 | NS | NS | NS | NS | NS | NS | NS |

$^{ab}$Means within a column of 3 or more independent variables lacking a common superscript differ significantly ($P < 0.05$)

Main effect means of breed and sex calculated using n = 200, main effect means of age calculated using n = 80.

SEM = Standard error of mean

TABLE 3

Effects of breed (Cobb or Ross), sex (Male or Female) and age on broiler blood carotene, aspartate aminotransferase (AST), creatine kinase (CK), bile acids (BA), uric acid (UA), total protein (TP), albumin (ALB), globulin (GLOB).

| Breed | Sex | Age | Carotene (mg/kg) | AST (U/L) | CK | BA (μmol/L) | UA (mg/dL) | TP | ALB (g/L) | GLOB |
|---|---|---|---|---|---|---|---|---|---|---|
| Cobb | | | 2.30 | 393.0 | 4359 | 11.37 | 6.3 | 3.06 | 2.33 | 0.73 |
| Ross | | | 2.30 | 392.3 | 4017 | 10.10 | 5.7 | 2.96 | 2.31 | 0.64 |
| P< | | | NS | NS | NS | NS | 0.003 | <0.001 | NS | <0.001 |
| | Male | | 2.17 | 386.7 | 4064 | 10.28 | 5.6 | 3.04 | 2.28 | 0.68 |
| | Female | | 2.42 | 398.0 | 4313 | 11.19 | 6.4 | 2.97 | 2.35 | 0.69 |
| | P< | | <0.001 | NS | NS | NS | <0.001 | 0.011 | 0.002 | NS |
| | | 14 d | 1.49$^{d}$ | 193.7$^{d}$ | 2401 | 12.6$^{a}$ | 6.2$^{b}$ | 2.67$^{c}$ | 2.20$^{b}$ | 0.45$^{c}$ |
| | | 21 d | 2.10$^{c}$ | 225.7$^{d}$ | 4908 | 13.4$^{a}$ | 6.2$^{b}$ | 2.95$^{b}$ | 2.36$^{a}$ | 0.59$^{b}$ |
| | | 28 d | 2.26$^{bc}$ | 335.6$^{c}$ | 5255 | 11.4$^{ab}$ | 6.3$^{b}$ | 2.97$^{b}$ | 2.31$^{a}$ | 0.64$^{b}$ |
| | | 35 d | 3.09$^{a}$ | 494.5$^{b}$ | — | 9.1$^{ab}$ | 6.9$^{b}$ | 3.25$^{a}$ | 2.39$^{a}$ | 0.87$^{a}$ |
| | | 42 d | 2.55$^{b}$ | 713.6$^{a}$ | — | 7.2$^{b}$ | 4.4$^{a}$ | 3.21$^{a}$ | 2.34$^{a}$ | 0.87$^{a}$ |
| | | P< | <0.001 | <0.001 | <0.001 | <0.001 | <0.001 | <0.001 | <0.001 | <0.001 |
| | | Linear P < | <0.001 | <0.001 | <0.001 | <0.001 | <0.001 | <0.001 | <0.001 | <0.001 |
| | | Quadratic P< | <0.001 | <0.001 | <0.001 | <0.001 | <0.001 | <0.001 | <0.001 | NS |
| Model Pooled SEM | | | 0.140 | 42.79 | 727 | 727 | 727 | 2.6 | 0.05 | 0.06 |
| Interaction Terms | | | | | | | | | | |
| Breed*Age | | | NS | NS | NS | NS | NS | 0.012 | NS | 0.100 |
| Sex*Age | | | NS | NS | NS | 0.068 | 0.002 | NS | 0.016 | NS |
| Breed*Sex | | | 0.058 | NS | NS | NS | NS | <0.001 | 0.050 | 0.048 |
| Breed*Age*Sex | | | NS | 0.023 | 0.020 | NS | NS | NS | NS | NS |

$^{ab}$Means within a column of 3 or more independent variables lacking a common superscript differ significantly ($P < 0.05$)

Main effect means of breed and sex calculated using n = 200, main effect means of age calculated using n = 80.

SEM = Standard error of mean

TABLE 4

Effects of breed (Cobb or Ross), sex (Male or Female) and age on blood mineral composition of broiler chickens fed a nutritionally adequate corn/soy-based diet.

| Breed | Sex | Age | vGlu (mg/dL) | iGlu | TCO2 (mmol/L) | HCT (%) | MDA (μM) | H | L | H:L |
|---|---|---|---|---|---|---|---|---|---|---|
| Cobb | | | 235 | 240 | 24.9 | 20.1 | 0.84 | 2175 | 8743 | 0.25 |
| Ross | | | 239 | 241 | 24.7 | 19.8 | 0.78 | 2421 | 9583 | 0.25 |
| P< | | | NS | NS | NS | NS | 0.047 | 0.10 | 0.02 | NS |
| | Male | | 239 | 243 | 25.1 | 19.5 | 0.81 | 2180 | 8711 | 0.25 |
| | Female | | 234 | 237 | 24.4 | 20.3 | 0.81 | 2416 | 9615 | 0.25 |
| | P< | | 0.033 | 0.008 | 0.006 | 0.052 | 0.883 | 0.11 | 0.010 | NS |
| | | 14 d | $235^{ab}$ | 243 | 23.5 | 18.9 | 1.14 | 1978 | 6924 | $0.28^{ab}$ |
| | | 21 d | $240^{ab}$ | 239 | 24.5 | 19.0 | 1.12 | 2912 | 9165 | $0.32^{a}$ |
| | | 28 d | $242^{a}$ | 244 | 25.1 | 20.5 | 0.63 | 2777 | 10720 | $0.26^{bc}$ |
| | | 35 d | $238^{ab}$ | 240 | 26.3 | 21.6 | 0.48 | 1182 | 6388 | $0.15^{d}$ |
| | | 42 d | $231^{b}$ | 235 | 24.6 | 19.7 | 0.69 | 2640 | 12620 | $0.21^{c}$ |
| | | P< | 0.039 | 0.082 | <0.001 | <0.001 | <0.001 | <0.001 | <0.001 | <0.001 |
| | | Linear P< | NS | 0.042 | <0.001 | 0.005 | <0.001 | NS | <0.001 | <0.001 |
| | | Quadratic P< | 0.003 | NS | <0.001 | 0.0121 | <0.001 | NS | NS | NS |
| Model Pooled SEM | | | 6 | 5 | 0.6 | 0.9 | 0.07 | 332 | 774 | 0.03 |
| Interaction Terms | | | | | | | | | | |
| Breed*Age | | | NS | 0.074 | NS | 0.089 | <0.001 | NS | NS | NS |
| Sex*Age | | | NS | NS | 0.023 | NS | 0.77 | NS | NS | NS |
| Breed*Sex | | | NS | NS | NS | <0.001 | NS | NS | NS | NS |
| Breed*Age*Sex | | | NS | NS | NS | NS | NS | NS | NS | NS |

[ab]Means within a column of 3 or more independent variables lacking a common superscript differ significantly (P < 0.05)

Main effect means of breed and sex calculated using n = 200, main effect means of age calculated using n = 80.

SEM = Standard error of mean

Example 2 (Early Diagnosis of Coccidiosis by Use of Blood Biomarker Combination)

The study of example 2 shows that, in a healthy environment, coccidiosis vaccinated birds perform poorer than unvaccinated birds. The possibility of early diagnosis of coccidiosis renders unnecessary vaccination superfluous and thereby boosts performance to the desired level. The study of example 2 also shows that the combination of Na, K, GLOB and/or carotenoid biomarker allows for a precise and early identification of the occurrence of coccidiosis in a broiler population. Early diagnosis allows for early intervention such that performance losses associated with coccidiosis can be successfully mitigated.

Facilities and Rearing

A total of 960 Cobb 500 male broiler chicks were obtained from the resident broiler breeder flock (North Carolina State University, Raleigh, NC) and randomly allocated to 48 pens (20 chicks per pen). The experiment comprised two factors, being without or with coccidial vaccination (d1[2]; vaccination available at Merck B-52 Coccivac, Merck & Co, Kenilworth, NJ) and without or with a coccidial challenge (d7[3]; 10× dose of the same vaccine used on d1 delivered via oral gavage), generating a total of four experimental treatments. The Merck B-52 coccidial vaccine contains live oocysts from *Eimeria acervulina, Eimeria maxima, Eimeria maxima* MFP, *Eimeria* mivati and *Eimeria tenella*. A common starter (d1-14) and grower (d15-35) diet was fed to all pens (cf. below Table 5) on an ad libitum basis. Water was also available ad libitum. Temperature was set at 95° F. for the first 12 hours and was subsequently reduced by 1° F. per day until 70° F. was reached, at which point this temperature was maintained for the remainder of the experiment. Photoperiod was 23 hours light for the first 6 days and was gradually reduced to 16 hours by the end of the experiment.

[2] vaccination at day 1, abbreviated as "d1"; this applies mutatis mutandis the other uses of the abbreviation "d" for "day" in this document

[3] challenge at day 7, abbreviated as "d7"; this applies mutatis mutandis the other uses of the abbreviation "d" for "day" in this document

TABLE 5

Composition (%) and calculated nutrient provision (%, unless otherwise stated) of the starter and grower diets.

| | Starter[4] | Grower[5] |
|---|---|---|
| Ingredients | | |
| Corn | 57.65 | 63.90 |
| Soybean meal (48% CP) | 32.02 | 23.89 |
| Poultry by-product meal | 5.00 | 5.86 |
| Poultry fat | 2.00 | 2.51 |
| Dicalcium phosphate (18.5% P) | 1.24 | 1.16 |
| Limestone | 0.61 | 0.82 |
| Salt | 0.50 | 0.50 |
| Choline chloride (60%) | 0.20 | 0.20 |
| Vitamin premix[1] | 0.05 | 0.05 |
| Mineral premix[2] | 0.20 | 0.20 |
| Selenium premix[3] | 0.05 | 0.05 |
| DL-Methionine | 0.23 | 0.17 |
| L-Lysine | 0.14 | 0.20 |
| L-Threonine | 0.11 | 0.09 |
| Total | 100.00 | 100.00 |
| Calculated nutrient content | | |
| Crude protein | 23.00 | 20.00 |
| Calcium | 0.90 | 0.90 |
| Available phosphorus | 0.45 | 0.45 |
| Potassium | 0.88 | 0.93 |
| Total lysine | 1.31 | 1.14 |
| Total methionine | 0.59 | 0.49 |
| Total threonine | 0.88 | 0.76 |
| Total methionine + cysteine | 0.95 | 0.81 |
| Sodium | 0.22 | 0.22 |
| Metabolizable energy (kcal/g) | 2,935 | 3,050 |

[1]Vitamin premix supplied the following per kg of diet: 13,200 IU vitamin A, 4,000 IU vitamin $D_3$, 33 IU vitamin E, 0.02 mg vitamin $B_{12}$, 0.13 mg biotin, 2 mg menadione ($K_3$), 2 mg thiamine, 6.6 mg riboflavin, 11 mg d-pantothenic acid, 4 mg vitamin $B_6$, 55 mg niacin, and 1.1 mg folic acid.

[2]Mineral premix supplied the following per kg of diet: manganese, 120 mg; zinc, 120 mg; iron, 80 mg; copper, 10 mg; iodine, 2.5 mg; and cobalt, 1 mg.

[3]Selenium premix provided 0.2 mg Se (as $Na_2SeO_3$) per kg of diet.

[4]Starter diet was fed to 14 d of age.

[5]Grower diet was fed from 15 to 35 d of age.

Negative Effect of Vaccination on Performance of Healthy Birds

Body weight (BW) and feed conversion ratio (FCR) per pen was recorded on d 7, 14, 21, 28 and 35. Mortality was monitored daily and the weights of any dead birds were used to correct the measured FCR values. The effect of coccidial challenge and vaccination on the feed conversion ratio is shown in Table 6. Feed conversion ratio (FCR) is a rate measuring the efficiency with which an animal convert animal feed into the desired output (e.g. the flesh). FCR is the mass of the input divided by the output. Thus, a high FCR is an indication for poor performance, i.e. a high FCR is undesirable. As shown in Table 6, administering a coccidial vaccination, without subsequent challenge, increased feed conversion ratio (FCR).

TABLE 6

Effect of coccidial challenge and vaccination on the feed conversion ratio (FCR; g:g) and mortality (%) of broiler chickens from d 1-35.

| Vaccine | Challenge | FCR d 1-7 | FCR d 1-14 | FCR d 1-21 | FCR d 1-28 | FCR d 1-35 | Mortality d 1-35, % |
|---|---|---|---|---|---|---|---|
| Treatment Effects | | | | | | | |
| – | + | 0.048 | 1.51 | 1.57 | 1.58 | 1.63 | 19.1 |
| – | – | 0.048 | 1.23 | 1.31 | 1.42 | 1.51 | 2.4 |
| + | + | 0.048 | 1.38 | 1.41 | 1.48 | 1.55 | 2.4 |
| + | – | 0.048 | 1.24 | 1.40 | 1.49 | 1.56 | 8.9 |
| P< | | NS | 0.001 | 0.001 | 0.001 | 0.001 | 0.05 |
| SEM | | 0.001 | 0.030 | 0.022 | 0.017 | 0.011 | 0.06 |
| Interaction Terms | | | | | | | |
| Vaccine*Challenge | | NS | 0.05 | 0.001 | 0.001 | 0.001 | 0.05 |

Abbreviation "d" is used for day.
The lower the P value the better; any P value below 0.05 is considered statistically significant.
NS = not statistically significant.
The notation with "*" means interaction, i.e. describes a situation in which the effect of one causal variable on an outcome depends on the state of a second causal variable.
g:g refers to grams of feed intake per gram of weight gain Birds with vaccine (+) but without challenge (–) had an FCR d1-35 (cumulative FCS, total feed intake and total weight gain over 1-35d) of 1.56 whereas birds without vaccine (–) and without challenge (–) a had a lower (i.e. better) FCR d1-35 of 1.51. Thus, in the absence of a challenge, a vaccination has a negative effect on performance. This also applies to mortality. The poorer performance of the vaccinated birds in the current study is in-line with previous observations and is clearly undesirable. According to a preferred embodiment of the present invention, unnecessary vaccination of healthy birds is preferably replaced by early intervention triggered by early diagnosis of coccidiosis.

Analysis of Blood Biochemistry

On day 6, 8, 13, 20, 27 and 34 one bird per pen was randomly selected, removed from the pen, euthanized and subjected to blood sampling via the vena cava.

Heparinized blood (approximately 0.2 ml) was analyzed in the i-Stat® Alinity v handheld blood analyzer fitted with a Chem8+ cartridge (Abbott Point of Care Inc., Princeton, NJ), which measured hematocrit (HCT), ionized calcium (Ca), glucose (GLU), chloride (Cl), sodium (Na), potassium (K), total carbon dioxide ($TCO_2$) and anion gap (AnGap).

Remaining heparinized blood (0.1 ml) was analyzed in the Vetscan® VS2 Chemistry Analyzer (Abaxis, inc) using the Avian/Reptilina Profile Plus cartridge (Abbott Point of Care Inc., Princeton, NJ). This resulted in aspartate aminotransferase (AST), creatine kinase (CK), uric acid (UA), GLU, Ca, phosphorus (P), total protein (TP), albumin (ALB), albumin/globulin (GLOB), potassium (K) and sodium (Na).

By selection of the above-mentioned cartridges, some of the blood parameter can be measured by both devices (i-Stat® and Vetscae®; superscripts for refer to either VetScan 'v' or iStat 'i' devices that were used). Other blood parameters can be measured with one of two devices only, given the indicated selection of cartridges. Below Table 7 gives an overview of parameters that can be measured with both devices:

TABLE 7

| Blood Parameter | i-Stat ® Alinity[4] v handheld blood analyzer fitted with a Chem8+ cartridge | Vetscan ® VS2[5] Chemistry Analyzer (Abaxis, Inc) using the Avian/ Reptilina Profile Plus cartridge |
|---|---|---|
| calcium (electrolyte) | + ($^i$Ca) | + ($^v$Ca) |
| glucose | + ($^i$Glu) | + ($^v$Glu) |
| chloride (electrolyte) | + ($^i$Cl) | + ($^v$Cl) |
| sodium (electrolyte) | + ($^i$Na) | + (vNa) |
| potassium (electrolyte) | + ($^i$K) | + ($^v$K) |

[4]For details, see "cartridge and test information", Rev. Date: 15, Aug. 2016, Art: 714258-01O, available at Abbott
[5]For details, see "Operator's Manual VertScanVS2", dated February 2009, available at Abaxis, Inc., Union City, CA 94587; Customer and Technical Service: 1-800-822-2947

Even though not explicitly mentioned, it is be understood that in the context of the present invention, Ca, Cl, Na and K refers to electrolytes, i.e. to ions.

Where the same blood parameter was measured with more than one device (e.g. Na or K), there was generally close agreement with respect to the observed treatment effect trajectory although the absolute values differed slightly. The units recorded by the two devices may differ though.

Precisely 1.0 ml of EDTA blood was mixed with 0.20 ml cellular fixant (Transfix®, MBL International), stored and shipped on wet ice to Cayman Analytical Laboratories (Ann Arbor, MI) for heterophil (HET) to lymphocyte (LYM) ratio analysis using flow cytometry as described by Lentfer et al. and Bilkova et al. (Lentfer, T. L., H. Pendl, E. K. F. Fröhlich, E. Von Borell, H. Pendl, and E. K. F. Fröhlich. 2015. H/L ratio as a measurement of stress in laying hens—methodology and reliability. Br. Poult. Sci. 56:157-163; Bílková, B., Z. Bainova, J. Janda, and M. Vinkler. 2017. Different breeds, different blood: Cytometric analysis of whole blood cellular composition in chicken breeds. Vet. Immunol. Immunopathol. 188:71-77).

Whole blood (3 ml) was spun and serum removed and stored on wet ice. 0.40 ml serum was used for total carotenoids (CAR) using the iCheck® carotene photometer device and test kit (BioAnalyt GmbH, Potsdam, Germany) as described by Kawashima et al. (Kawashima, C., S. Nagashima, K. Sawada, F. J. Schweigert, A. Miyamoto, and K. Kida. 2010. Effect of β-Carotene Supply During Close-up Dry Period on the Onset of First Postpartum Luteal Activity in Dairy Cows. 287:282-287). Remaining serum was frozen on dry ice and shipped to Cayman Analytical Laboratories (Ann Arbor, MI) for thiobarbituric acid (TBARS) analysis (Wills, E. D. 1966. Mechanisms of lipid peroxide formation in animal tissues. Biochem. J. 99: 667-676), which measures malondialdehyde (MDA) in the blood.

An overview of the analysis of blood biochemistry done in example 2 is shown in below Table 8:

TABLE 8

| Sample category | Type of sample | tested blood parameters | Device/Laboratory |
|---|---|---|---|
| 1 | heparinized blood | Ca, P, Cl, Na, K, TP, GLOB, TCO2 and others | Vetscan ® VS2 Chemistry Analyzer and/or i-Stat ® Alinity v handheld blood analyzer |
| 2 | EDTA treated blood | HET, LYM and HET:LYM | Cayman Analytical Laboratories (Ann Arbor, MI) |
| 3 | serum collection tube | total carotenoids (mg/kg); TBARS (malondialdehyde; MDA) | iCheck ® carotene photometer Cayman Analytical Laboratories (Ann Arbor, MI) |

Age dependent blood parameters useful for early diagnosis of coccidiosis Statistical analysis of the study of Example 2 revealed that day 13 (13 days post-hatch) is the age at which the biomarker responses to coccidiosis challenge were most acute. At ages below day 7 and at ages above day 21, the biomarker responses to coccidiosis challenge was not useful for early diagnosis of coccidiosis. Ages from day 10 and day 16 are expected to be very useful for early diagnosis of coccidiosis. Statistically, the highest diagnostic precision is achieved at day 13.

Blood parameters useful for early diagnosis of coccidiosis Statistical analysis of study of Example 2 shows that on day 13, there are specific biomarkers that are significantly influenced by coccidial challenge.

Alternative biomarkers were not significantly influenced (e.g. there was no effect of coccidial challenge on plasma Ca[6], P[7], and Cl[8]). Below Table 9 shows the responses to coccidial challenge, on d13, for a sub-set of specific blood

[6] calcium (Ca); analysis of heparinized blood

[7] phosphorus (P); analysis of heparinized blood

[8] chloride (Cl); analysis of heparinized blood parameters. These are the blood parameters that can be used for early diagnosis of coccidiosis. Any P value below 0.05 is considered statistically significant.

TABLE 9

| Blood parameter | Na | K | GLOB | AnGap[9] (calculated Anion Gap) | Car (Carotenoids) |
|---|---|---|---|---|---|
| Age of bird when blood sample was taken | Day 13 | Day 13 | Day 13 | Day 13 | Day 13 |
| Device used for analysis of blood sample | i-Stat ® Alinity with Chem8+ cartridge | i-Stat ® Alinity with Chem8+ cartridge | Vetscan ® VS2 Chemistry Analyzer with Avian/Reptilina Profile Plus cartridge | i-Stat ® Alinity with Chem8+ cartridge | iCheck ® carotene photometer device |

TABLE 9-continued

| Blood parameter | Na | K | GLOB | AnGap[9] (calculated Anion Gap) | Car (Carotenoids) |
|---|---|---|---|---|---|
| non-challenge | 144.4 mmol/l | 5.06 mmol/l | 0.43 g/l | 19.6 mmol/l | 0.91 ppm |
| coccidiosis challenge | 140.7 mmol/l | 6.10 mmol/l | 0.73 g/l | 17.2 mmol/l | 0.40 ppm |
| P value | P < 0.001 | P < 0.001 | P < 0.001 | P < 0.01 | P < 0.001 |
| Model for clinical or pre-clinical diagnosis of coccidiosis | Value for Na parameter measured at d 13 post-hatch lower than pre-determined range | Value for K parameter measured at d 13 post-hatch higher than pre-determined range | Value for GLOB parameter measured at d 13 post-hatch higher than pre-determined range | Value for AnGap parameter measured at d 13 post-hatch lower than pre-determined range | Value for Carotenoids parameter measured at d 13 post-hatch lower than pre-determined range |

[9]Anion Gap is calculated in CHEM8+ cartridges as follows: Anion Gap (CHEM8+) = (Na + K) − (Cl + (TCO2 − 1)) cf. publication "$PCO_2$ AND CALCULATED VALUES FOR $HCO_3$, BASE EXCESS AND ANION GAP" available at Abaxis, Art: 714182-00V, Rev. Date 29 Sep. 2017; https://www.abaxis.com/sites/default/files/resource-packages/PCO2%20CTI%20Sheet%20714182-00V.pdf Thus, (i) measuring higher than normal (baseline) Na, K and/or GLOB on d13 and/or (ii) measuring a lower than normal (baseline) AnGap and/or Car on d13 is an indication of coccidiosis in the respective broiler population. After such indication, a suitable intervention is recommended such that performance losses associated with coccidiosis can be successfully mitigated. Surprisingly, the same conclusion could not have been reached with the same precision or could not have been reached at all if the blood sample had been taken when the bird was younger than 7 days or older than 21 day. At ages from day 10 and day 18, the same conclusion could have been reached, although not with the same precision as on day 13.

Improved Precision of Early Diagnosis of Coccidiosis

Statistical analysis of study of Example 2 shows that prediction of coccidiosis using blood analysis can be improved by the simultaneous use of more than one biomarker. For example, when using K as only pre-determined blood parameter, a Receiver Operating Characteristic (ROC) analysis of the interaction between bird age and K delivers an area under the curve (AUC) of 0.62 (i.e. 62% separation between challenged and non-challenged birds). A mixed model with multiple pre-determined blood parameters including carotenoids, GLOB, ANGAP and K with the age of the bird as an interactive term delivers a ROC AUC of 0.82 (i.e. 82% accurate separation between challenged and non-challenged birds).

In the most preferred embodiment of the present invention, a very high ROC AUC of 0.89 is achieved; in the most preferred embodiment, the pre-determined following blood parameters are used: AST[10], PHOS, GLOB, carotenoids, K, ANGAP and TCO2, including the interaction with age.

[10] blood aspartate aminotransferase (AST)

Statistical analysis of study of Example 2 shows very clearly that when taking into consideration (i) more than 1 pre-determined blood parameter (preferably 3 to 6 pre-determined blood parameters) and (ii) the age of the bird, coccidiosis can be diagnosed at early stage with accurate diagnostic precision.

Thus, Example 2 shows that collection of specific data at a specific moment in time offers a biochemical 'fingerprint' of coccidiosis allowing to achieve an objective early diagnosis.

Further Evidence for the Age Dependency (Veterinary Necropsy)

The bird randomly selected on day 6, 8, 13, 20, 27 and 34 was not only subjected to blood sampling. After euthanization, it was also subjected to veterinary necropsy. Veterinary post-mortem analysis was specifically oriented toward metrics that were known to be associated with coccidiosis, specifically gross *acervulina* (GAc), gross *tenella* (GTn), gross micro max (GMx) and micro max (mMx). These observations have a score from 0 to 4 with 0 being 'absent' and 4 being 'severe' as described by Conway et al. (Conway, D. P. and M. E. McKenzie. 2007. Poultry coccidiosis: diagnostic and testing procedures. 3rd Edition. Blackwell Publishing Professional, Ames, Iowa, USA. pp. 7-20).

In the study of Example 2, birds that were not vaccinated but challenged had higher GAc scores on day 13 than was the case for alternative treatment groups, resulting in a significant challenge*vaccination*age interaction. This confirms the importance of day 13. The same challenge*vaccination*age interaction could not be observed on or before day 8. Similarly, the same challenge*vaccination*age interaction could not be observed on or after day 20.

Example 3 (Administration of a Microbial Muramidase to Feed as a Response to an Avian Disease)

The results obtained in the study of Example 3 shows that broiler chickens which were infected by *Eimeria* and *Clostridium* perfringes can effectively be treated by the inclusion of microbial muramidase in animal feed. Adding microbial muramidase to animal feed is therefore one manner to adapt nutrition after early diagnosis of an avian disease.

Materials and Methods

Center of Immune Response in Poultry (CERIA) at Federal University of Parana. The birds were housed in the experimental room with negative pressure. Each replicate was in cages with sterilized litter, nipple drinkers, and automatic temperature control. Birds were raised with water and feed ad libitum.

Experimental Design—Treatments and Animals

The amount of 256 male broilers (01 to 28 days of age) were distributed in a completely randomized design divided into 04 treatments with 7 repetitions each, starting 8 birds in each repetition and 1 group control without challenge.

The birds were allocated in different rooms: with or without challenge.

8 rooms with 4 cages each:

1 room without challenge (experimental negative control)—4 cages with 8 birds (1 cage per treatment)—total: 32 birds;

7 rooms with a challenge (*Eimeria* and *C. perfringens*): In each room, 4 treatments were allocated and at the end, there is 7 replicates with 8 birds each—total: 224 birds.

TABLE 10

| Treatment | *Eimeria* challenge | *Clostridium* challenge | Product |
|---|---|---|---|
| CN | No | No | None |
| T1 | Yes | Yes | None |
| T2 | Yes | Yes | Muramidase (25 000 LSU/kg, 476 mg/kg) |
| T3 | Yes | Yes | Muramidase (35 000 LSU/kg, 667 mg/kg) |
| T4 | Yes | Yes | Enramycin 10 ppm (Enradin ® 8%) |

Muramidase: activity 52 500 FSU(F)/g

Challenge

In the first day of the trial, animals from T1, T2, T3, and T4 have received the anticoccidial vaccine 15 times the manufactured recommendation dose. In the 10th, 11th and 12th day of the experiment, they were inoculated with *Clostridium perfringens* (108 CFU/ml—isolated from the field Necrotic enteritis case) by gavage.

Performance

At 7, 14, 21 and 28 days of age, the feed and birds were weighted, and was evaluated feed intake (FI), body weight gain (BWG) and feed conversion ratio (FCR). The data were submitted to analysis of variance (ANOVA) and Tukey's test for the means with a significant difference (P<0.05). Data are listed as Tables 11 and 12.

From the above tables, *Eimeria* and *Clostridium perfringens* challenge significantly reduce the weight gain (16%) and Feed intake (3%) compared to the control (CN) without challenge. The groups T2 and T3 supplemented with muramidase had improved weight gain and FCR.

The invention claimed is:

1. A computer-implemented method for treating or preventing coccidiosis comprising:

receiving, by a computing device and from a point-of-care device, blood parameters that have been measured ex vivo in blood of at least one member of a group of birds;

providing a model which defines predetermined ranges of blood parameters indicative of birds suffering from coccidiosis, wherein the blood parameters indicative of the birds suffering from coccidiosis comprise at least three pre-determined blood parameters selected from a group consisting of sodium, potassium, globulin, carotenoid and anion gap;

analyzing, using the model, the blood parameters to determine if the group of birds is in need of an additive that treats or prevents coccidiosis;

based on the at least three pre-determined blood parameters falling outside the predetermined ranges and after a determination that the group of birds is in need of the additive, sending, by the computing device and to a user device, a recommendation for adding the additive to feed that treats or prevents coccidiosis; and administering, based on the recommendation and to the group of birds, an appropriate feed with the additive comprising one or more microbial muramidases to treat or prevent coccidiosis.

TABLE 11

Mean ± standard deviation of BWG—Body Weight Gain (g) at all periods.

| Treatment | 1-7 D | CV % | 1-14 D | CV % | 1-21 D | CV % | 1-28 D | CV % |
|---|---|---|---|---|---|---|---|---|
| CN | 154.04 ± 16.23 a | 21.973 | 563.13 ± 26.32 a | 9.348 | 1207.4 ± 107.08 a | 17.737 | 1858.1 ± 52.83 a | 5.687 |
| T1 | 88.114 ± 6.60 b | 19.846 | 412.95 ± 27.88 b | 17.866 | 923.61 ± 41.83 b | 11.985 | 1551.9 ± 49.55 b | 8.448 |
| T2 | 89.99 ± 5.47 b | 16.086 | 394.62 ± 18.70 b | 12.544 | 905.47 ± 25.39 b | 7.420 | 1566.7 ± 55.38 b | 9.352 |
| T3 | 107.96 ± 12.11 b | 29.684 | 389.94 ± 13.20 b | 8.956 | 939.34 ± 58.64 b | 16.519 | 1570.3 ± 37.43 b | 6.307 |
| T4 | 90.95 ± 5.11 b | 14.890 | 413.37 ± 12.89 b | 8.251 | 926.22 ± 23.58 b | 6.738 | 1595.5 ± 42.62 b | 7.067 |
| P value | 0.0005 | | 0.0001 | | 0.0049 | | 0.0097 | |

ab Mean with different letters in the same column are significantly different at P < 0.05 Tukey's test

TABLE 12

Mean ± standard deviation of FCR (Feed Conversion Ratio) at all periods.

| Treatment | 1-7 D | CV % | 1-14 D | CV % | 1-21 D | CV % | 1-28 D | CV % |
|---|---|---|---|---|---|---|---|---|
| CN | 1.101 ± 0.139 | 22.999 | 0.832 ± 0.017 | 4.097 | 1.052 ± 0.071 b | 13.503 | 1.150 ± 0.019 b | 3.362 |
| T1 | 1.504 ± 0.099 | 17.470 | 1.074 ± 0.062 | 15.439 | 1.345 ± 0.054 a | 10.628 | 1.332 ± 0.034 a | 6.791 |
| T2 | 1.496 ± 0.155 | 27.440 | 1.080 ± 0.044 | 10.992 | 1.322 ± 0.058 a | 11.601 | 1.290 ± 0.050 ab | 10.370 |
| T3 | 1.427 ± 0.195 | 36.284 | 1.035 ± 0.063 | 16.302 | 1.314 ± 0.060 a | 12.212 | 1.285 ± 0.020 ab | 4.143 |
| T4 | 1.568 ± 0.123 | 20.815 | 1.070 ± 0.049 | 12.256 | 1.255 ± 0.036 ab | 7.735 | 1.228 ± 0.024 ab | 5.240 |
| P value | 0.3816 | | 0.0811 | | 0.0250 | | 0.0229 | |

ab Mean with different letters in the same column are significantly different at P < 0.05 Tukey's test 2. The method of claim 1, wherein the additive is a feed additive that comprises the one or more microbial muramidases obtained or obtainable from phylum Ascomycota, or subphylum Pezizomycotina.

3. The method of claim 1, wherein the group of birds is a group of chickens of a single breed and a single age.

4. The method of claim 1, wherein the blood parameters have been measured ex vivo in the blood of chicken between 9 and 21 days old.

5. The method of claim 1, wherein the blood parameters comprise a total amount of carotenoids in blood serum that has been separated from whole blood.

6. The method of claim 1, wherein the model defines a predetermined range for each of the blood parameters, wherein determining that the group of birds is in need of the additive comprises:

determining that the at least three pre-determined blood parameters fall outside the corresponding predetermined range.

7. The method of claim 1, wherein the group of birds is a group of chickens of a single breed, a single age, and a single sex.

8. The method of claim 4, wherein the blood parameters have been measured in the blood of chicken between 10 and 18 days old.

9. The method of claim 4, wherein the blood parameters have been measured in the blood of chicken of 13 days old.

10. The method of claim 1, wherein analyzing the blood parameters comprises analyzing, in a specific breed of chicken, potassium or sodium in whole blood.

11. The method of claim 1, wherein analyzing the blood parameters comprises analyzing calcium in whole blood independent from a breed of chicken.

12. The method of claim 1, wherein analyzing, using the model, the blood parameters comprise:

providing, as input to the model, the blood parameters associated with the at least one member of the group of birds; and receiving, as output from the model, an indication whether the group of birds is in need of the additive that treats or prevents coccidiosis.

13. The method of claim 1, wherein the blood parameters depend on a state of causal variable, and wherein the causal variable is selected from a group consisting of heat stress, humidity, nutritional inadequacy, transport stress and exposure to a coccidial challenge.

14. The method of claim 1, wherein administering the appropriate feed with the additive comprising the one or more microbial muramidases comprises:

replacing a vaccination schedule of the group of birds with a schedule for administering the appropriate feed.

15. The method of claim 1, further comprising:

after determining, using the model, that a first group of birds associated with a first age is in need of the additive that treats or prevents coccidiosis, administering the appropriate feed with the additive comprising the one or more microbial muramidases; and after determining that a second group of birds is associated with a second age different from the first age, vaccinating the second group of birds with a coccidial vaccine.

16. A system for landless monogastric animal production for treating or preventing coccidiosis comprising:

at least one point-of-care device suitable for measuring values of blood parameters of at least one member of a group of birds;

at least one user device coupled to the at least one point-of-care device; and a computing device configured to:

receive, from the point-of-care device, blood parameters that have been measured ex vivo in blood of at least one member of a group of birds;

provide a model which defines predetermined ranges of blood parameters indicative of birds suffering from coccidiosis, wherein the blood parameters indicative of the birds suffering from coccidiosis comprise at least three pre-determined blood parameters selected from a group consisting of sodium, potassium, globulin, carotenoid and anion gap;

analyze, using the model, the blood parameters to determine if the group of birds is in need of an additive that treats or prevents coccidiosis;

based on the at least three pre-determined blood parameters falling outside the predetermined range and after a determination that the group of birds is in need of the additive, send, to the user device, a recommendation for adding the additive to feed that treats or prevents coccidiosis; and administering, based on the recommendation and to the group of birds, an appropriate feed with the additive comprising one or more microbial muramidases to treat or prevent coccidiosis.

17. The system of claim 16, wherein the additive is a feed additive that comprises the one or more microbial muramidases obtained or obtainable from phylum Ascomycota, or subphylum Pezizomycotina.

18. The system of claim 16, wherein the group of birds is a group of chickens of a single breed and a single age.

19. The system of claim 16, wherein the values of the blood parameters have been measured ex vivo in the blood of chicken between 9 and 21 days old.

20. The system of claim 19, wherein the blood parameters have been measured in the blood of chicken between 10 and 18 days old.

21. The system of claim 19, wherein the blood parameters have been measured in the blood of chicken of 13 days old.

* * * * *